US010220112B2

United States Patent
Solecki et al.

(10) Patent No.: US 10,220,112 B2
(45) Date of Patent: Mar. 5, 2019

(54) CYCLIC ANTIMICROBIAL PSEUDOPEPTIDES AND USES THEREOF

(71) Applicants: INSERM (INSTITUT NATIONAL DE LA SANTE ET DE LA RECHERCHE MEDICALE), Paris (FR); CENTRE NATIONAL DE LA RECHERCHE SCIENTIFIQUE—CNRS, Paris (FR); UNIVERSITE DE RENNES 1, Rennes (FR)

(72) Inventors: Olivia Solecki, Rennes (FR); Amor Mosbah, M'Saken (TN); Michèle Baudy-Floch, Rennes (FR); Brice Felden, Le loup du Lac (FR)

(73) Assignees: Universite de Rennes 1, Rennes (FR); Centre National de la Recherche Scientifique, Paris (FR); Institut National de la Sante et de la Recherche Medicale, Paris (FR)

( * ) Notice: Subject to any disclaimer, the term of this patent is extended or adjusted under 35 U.S.C. 154(b) by 0 days.

(21) Appl. No.: 15/523,261

(22) PCT Filed: Oct. 30, 2015

(86) PCT No.: PCT/EP2015/075213
§ 371 (c)(1),
(2) Date: Apr. 28, 2017

(87) PCT Pub. No.: WO2016/066784
PCT Pub. Date: May 6, 2016

(65) Prior Publication Data
US 2017/0319738 A1    Nov. 9, 2017

(30) Foreign Application Priority Data
Oct. 31, 2014   (EP) .................... 14191238

(51) Int. Cl.
| | | |
|---|---|---|
| *C07K 14/31* | (2006.01) | |
| *A61L 15/46* | (2006.01) | |
| *A61L 27/54* | (2006.01) | |
| *A61L 29/16* | (2006.01) | |
| *A61L 31/16* | (2006.01) | |
| *A61L 17/00* | (2006.01) | |
| *A61L 24/00* | (2006.01) | |
| *A61L 26/00* | (2006.01) | |

(52) U.S. Cl.
CPC ............. *A61L 15/46* (2013.01); *A61L 17/005* (2013.01); *A61L 24/0015* (2013.01); *A61L 26/0066* (2013.01); *A61L 27/54* (2013.01); *A61L 29/16* (2013.01); *A61L 31/16* (2013.01); *C07K 14/31* (2013.01); *A61L 2300/25* (2013.01); *A61L 2300/404* (2013.01)

(58) Field of Classification Search
None
See application file for complete search history.

(56) References Cited

U.S. PATENT DOCUMENTS

2004/0072990 A1    4/2004   Tzeng et al.

FOREIGN PATENT DOCUMENTS

| WO | WO 2013/050590 | * | 4/2013 |
| WO | WO 2013/050590 A1 | | 4/2013 |

OTHER PUBLICATIONS

Wessolowski et al., J Pept Res. Oct. 2004;64(4):159-69 (Year: 2004).*
Olivia Solecki et al, "Converting a *Staphylococcus aureus* Toxin into Effective Cyclic Pseudopeptide Antibotics", Chemistry & Biology, vol. 22, No. 3; Mar. 19, 2015.

* cited by examiner

*Primary Examiner* — Sergio Coffa
(74) *Attorney, Agent, or Firm* — Morgan, Lewis & Bockius LLP

(57) ABSTRACT

The present invention provides cyclic antimicrobial pseudopeptides that are useful in a variety of applications. Also provided are pharmaceutical compositions, products and kits comprising such cyclic antimicrobial peptides and methods of using these antimicrobial peptides for modifying infectivity, killing microorganisms or inhibiting microbial growth or function and for preventing and/or treating an infection or contamination caused by such microorganisms.

3 Claims, 4 Drawing Sheets
Specification includes a Sequence Listing.

CYCLIC ANTIMICROBIAL PSEUDOPEPTIDES AND USES THEREOF

RELATED PATENT APPLICATIONS

The present application is filed pursuant to 35 U.S.C. § 371 as a U.S. National Phase Application of International Patent Application No. PCT/EP2015/075213, which was filed on Oct. 30, 2015, claiming the benefit of priority to European Patent Application No. EP 14 191 238 filed on Oct. 31, 2014. The content of each of the aforementioned Patent Applications is incorporated herein by reference in its entirety.

BACKGROUND OF THE INVENTION

Antimicrobial peptides represent widely distributed, ancient weapons, produced by living organisms to defend themselves against a variety of rivals, for survival and spread. Plant and animal, antimicrobial peptides are part of their innate immune defenses. Antimicrobial peptides are also produced by various microorganisms including bacteria, termed bacteriocins (Hassan et al., J. Appl. Microbiol., 2012, 113: 723-736). Antimicrobial peptides provide advantages for the producer against competing bacteria in the environment or during infections. To defeat the invading or competing microorganisms, the antimicrobial peptides target a fundamental difference between the membranes of prokaryotes and of eukaryotes (Zasloff, Nature, 2002, 415: 389-395). The exposed surfaces of bacterial membranes are populated by negatively charged phospholipids whereas the outer leaflet of plants and animals membranes is composed of neutral lipids. Eukaryotic and prokaryotic antimicrobial peptides share common features: they are small (20 to 50 amino acids), cationic, amphiphilic or hydrophobic, facilitating their interactions with the negatively charged bacterial membranes on which they can form pores causing leakage of cellular solutes or disrupt membrane integrity, triggering cell death (Melo et al., Nat. Rev. Microbiol., 2009, 7: 245-250).

Various bacteria have also the ability to produce toxic peptides from toxin-antitoxin modules in response to environmental stimuli including persister cells formation, stress resistance, protection against viral infections or biofilm formation (Ghafourian et al., Curr. Issues Mol. Biol., 2013, 16: 9-14). Type I toxin-antitoxin pairs encode hydrophobic toxic peptides whose synthesis is repressed by antisense RNAs during growth, and they are widely distributed in bacteria (Fozo et al., Nucleic Acids Res., 2010, 38: 3743-3759; Pinel-Marie et al., Cell Rep., 2014, 7: 424-435). Functional Type I toxin-antitoxin pairs expressed by *Staphylococcus aureus*, a major human pathogen, have been identified (Sayed et al., Nat. Struct. Mol. Biol., 2011, 19: 105-112). The RNA pair lies on opposite strands, one RNA encodes a 30-residue PepA1 toxic peptide and the other convergent antisense RNA inhibits toxin production by preventing its synthesis. PepA1 structure was solved by NMR spectroscopy and is a long bent, interrupted helix, presumably forming pores to alter membrane integrity. In vivo, PepA1 localizes at the bacterial membrane, triggers *S. aureus* death and also lyses human erythrocytes at similar concentrations (Sayed et al., J. Biol. Chem., 2012, 287: 43454-43463). Considerable efforts are currently implemented to develop modified antimicrobial peptides as anti-infective agents (Wilmes and Sahl, Int. J. Med. Microbiol., 2014, 304: 93-99), especially because of the alarming emergence of pathogens resistant to various drugs used in clinics. Natural antimicrobial peptides act rapidly and locally and cannot be used as therapeutics because of their degradations by numerous proteases.

The present Applicant has previously reported peptides derived from the SprA1-encoded bacteriocin isolated from *Staphylococcus aureus* with antimicrobial properties (WO 2013/050590). However, these peptides had the disadvantage of having cytolytic properties

SUMMARY OF THE INVENTION

The present invention provides cyclic peptides which exhibit strong antimicrobial properties and tremendous stability in human body fluids such as serum, but which are devoid of toxicity on human cells.

Accordingly, in one aspect, the present invention provides a cyclic antimicrobial peptide having an amino acid sequence selected from the group consisting of SEQ ID NOs: 1-14, or an antimicrobial variant thereof.

In another aspect, the present invention relates to a cyclic peptide as described herein for use as a therapeutic agent, in particular as an antimicrobial agent.

In another aspect, the present invention provides a pharmaceutical composition comprising an effective amount of at least one cyclic antimicrobial peptide as described herein, and a pharmaceutically acceptable carrier or excipient.

In a related aspect, the present invention relates to the use of a cyclic antimicrobial peptide as described herein for the manufacture of a medicament, in particular a medicament intended to be used as an antimicrobial agent.

The invention also provides a product comprising at least one cyclic antimicrobial peptide as described herein or a pharmaceutical composition thereof, wherein the product is selected from the group consisting of bandages, plasters, sutures, adhesives, wound dressings, implants, contact lenses, cleaning solutions, storage solutions, cleaning products, personal care products, and cosmetics.

In still another aspect, the present invention provides a method for preventing or treating a microbial infection in a subject, the method comprising a step of: administering to said subject an effective amount of at least one cyclic antimicrobial peptide as described herein or a pharmaceutical composition thereof.

In certain embodiments, the microbial infection is caused by a gram-negative bacterium or by a gram-positive bacterium. In particular, the gram-negative bacterium may be a bacterium of the *Bordetella, Salmonella, Enterobacter, Klebsiella, Shigella, Yersinia, Escherichia coli, Vibrio, Pseudomonas, Neisseria, Haemophilus*, or *Agrobacterium* genus. The gram-positive bacterium may be a bacterium of the *Staphylococcus, Micrococcus, Lactococcus, Lactobacillus, Clostridium, Bacillus, Streptococcus, Enterococcus*, or *Listeria* genus.

The therapeutic methods according to the present invention may be applied to humans or other mammals. In certain preferred embodiments, the subject is human.

In yet another aspect, the present invention provides a method for preventing or eliminating microbial contamination of the surface of an object, said method comprising a step of: contacting the surface of said object with an effective amount of at least one one cyclic antimicrobial peptide as described herein or a composition thereof.

In certain embodiments, the microbial contamination of the surface of the object is caused by a gram-negative bacterium or by a gram-positive bacterium. The gram-negative bacterium may be a bacterium selected from the group consisting of bacteria of the genus *Salmonella*, bacteria of the genus *Shigella*, and bacteria of the genus *Escherichia*. The gram-positive bacterium may be a bacterium of the genus *Staphylococcus*.

In certain embodiments, the object to which the decontamination method is applied is selected from sutures, implants, contact lenses, catheters, syringes, and gloves.

In a related aspect, the present invention relates to a cleaning solution or cleaning product comprising at least one cyclic antimicrobial peptide as described herein. The cleaning product may be a cleaning pad or a cleaning wipe.

These and other objects, advantages and features of the present invention will become apparent to those of ordinary skill in the art having read the following detailed description of the preferred embodiments.

DEFINITIONS

Figure 1:
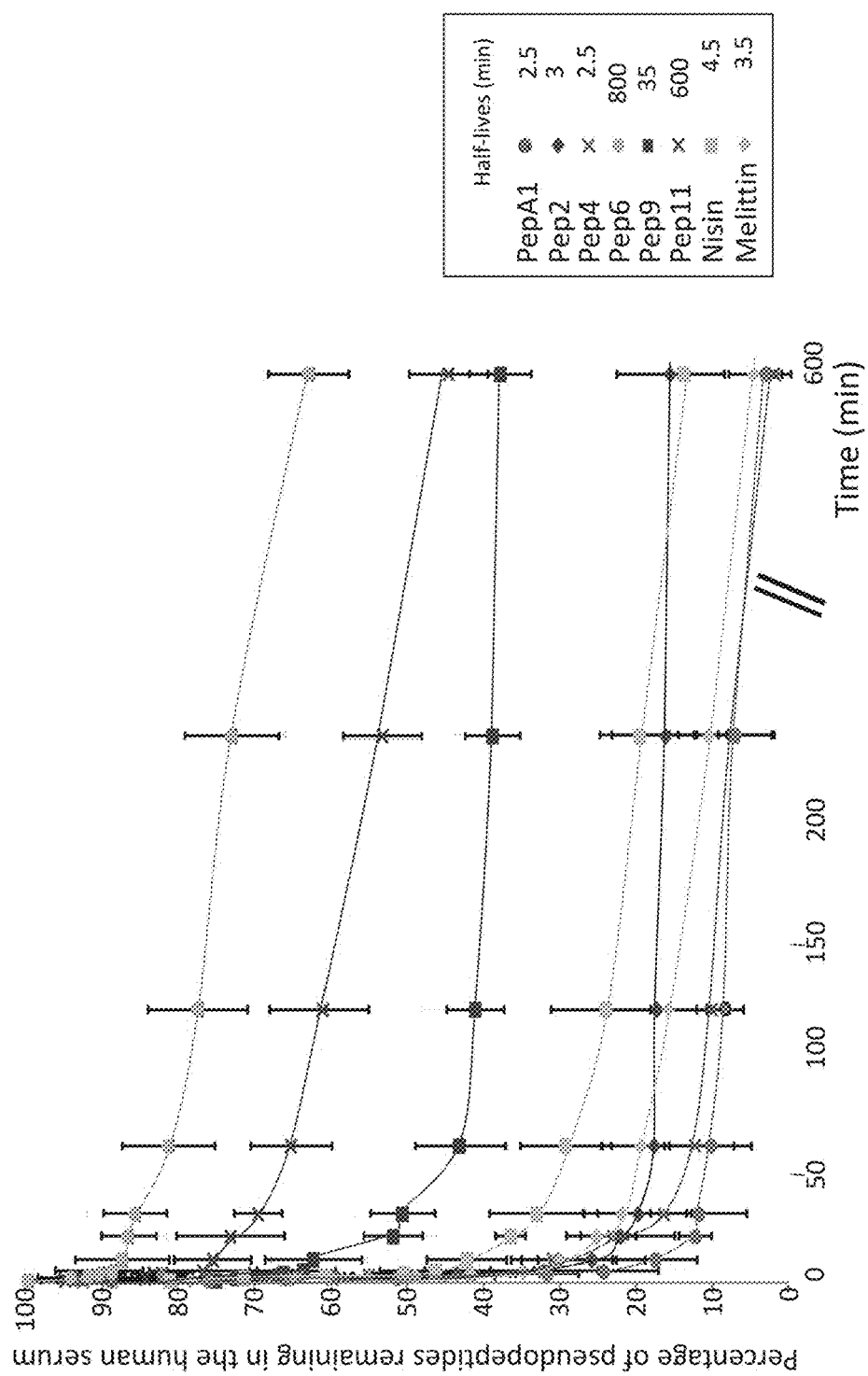
FIG. 1. Degradation kinetics of the antibacterial peptides in human serum. The respective amounts and half-lives of the peptides were determined by HPLC analysis, from 0 to 10 hours incubations in human serum. Inset: Identities (sign and color codes) and half-lifes of the peptides tested. The half-life of PepA1 primary peptide was considerably enhanced, up to ~800 min (Pep6).

Throughout the specification, several terms are employed that are defined in the following paragraphs.

As used herein, the term "subject" refers to a human or another mammal primate, mouse, rat, rabbit, dog, cat, horse, cow, pig, camel, and the like). In many embodiments of the present invention, the subject is a human being. In such embodiments, the subject is often referred to as an "individual" or a "patient". The terms "individual" and "patient" do not denote a particular age.

The term "treatment" is used herein to characterize a method or process that is aimed at (1) delaying or preventing the onset of a disease or condition; (2) slowing down or stopping the progression, aggravation, or deterioration of the symptoms of the disease or condition; (3) bringing about amelioration of the symptoms of the disease or condition; or (4) curing the disease or condition. A treatment may be administered prior to the onset of the disease or condition, for a prophylactic or preventive action. Alternatively or additionally, a treatment may be administered after initiation of the disease or condition, for a therapeutic action.

A "pharmaceutical composition" is defined herein as comprising an effective amount of at least one cyclic antimicrobial peptide according to the invention, and at least one pharmaceutically acceptable carrier or excipient.

As used herein, the term "effective amount" refers to any amount of a compound (e.g., a cyclic antimicrobial peptide), agent, antibody, or composition that is sufficient to fulfil its intended purpose(s), e.g., a desired biological or medicinal response in a cell, tissue, system or subject.

The term "pharmaceutically acceptable carrier or excipient" refers to a carrier medium which does not interfere with the effectiveness of the biological activity of the active ingredient(s) and which is not excessively toxic to the host at the concentration at which it is administered. The term includes solvents, dispersion, media, coatings, antibacterial and antifungal agents, isotonic agents, and adsorption delaying agents, and the like. The use of such media and agents for pharmaceutically active substances is well known in the art (see for example "*Remington's Pharmaceutical Sciences*", E. W. Martin, 18th Ed., 1990, Mack Publishing Co.: Easton, Pa., which is incorporated herein by reference in its entirety). In certain embodiments, the pharmaceutically acceptable carrier or excipient is a veterinary acceptable carrier or excipient.

The terms "protein", "polypeptide", and "peptide" are used herein interchangeably, and refer to amino acid sequences of a variety of lengths, either in their neutral (uncharged) forms or as salts, and either unmodified or modified for example by glycosylation, side-chain oxidation, or phosphorylation. In certain embodiments, the amino acid sequence is a full-length native protein. In other embodiments, the amino acid sequence is a smaller fragment of the full-length protein. In still other embodiments, the amino acid sequence is modified by additional substituents attached to the amino acid side chains, such as glycosyl units, lipids, or inorganic ions such as phosphates, as well as modifications relating to chemical conversions of the chains such as oxidation of sulfhydryl groups. Thus, the term "protein" (or its equivalent terms) is intended to include the amino acid sequence of the full-length native protein, or a fragment thereof, subject to those modifications that do not significantly change its specific properties. In particular, the term "protein" encompasses protein isoforms, i.e., analogs that are encoded by the same gene, but that differ in their pI or MW, or both. Such isoforms can differ in their amino acid sequence (e.g., as a result of allelic variation, alternative splicing or limited proteolysis), or in the alternative, may arise from differential post-translational modification (e.g., glycosylation, acylation, phosphorylation).

The terms "analog" and "variant" are used herein interchangeably. When used in reference to a protein or protein portion, these terms refer to a polypeptide that possesses a function similar or identical to that of the protein or protein portion but need not necessarily comprise an amino acid sequence that is similar or identical to the amino acid sequence of the protein or protein portion or a structure that is similar or identical to that of the protein or protein portion. Preferably, in the context of the present invention, a protein analog has an amino acid sequence that is at least 30%, more preferably, at least 35%, 40%, 45%, 50%, 55%, 60%, 65%, 70%, 75%, 80%, 85%, 90%, 95% or 99% identical to the amino acid sequence of the protein or protein portion.

The term "homologous" (or "homology"), as used herein, is synonymous with the term "identity" and refers to the sequence similarity between two polypeptide molecules or between two nucleic acid molecules. When a position in both compared sequences is occupied by the same base or same amino acid residue, the respective molecules are then homologous at that position. The percentage of homology between two sequences corresponds to the number of matching or homologous positions shared by the two sequences divided by the number of positions compared and multiplied by 100. Generally, a comparison is made when two sequences are aligned to give maximum homology. Homologous amino acid sequences share identical or similar amino acid sequences. Similar residues are conservative substitutions for, or "allowed point mutations" of, corresponding amino acid residues in a reference sequence. "Conservative substitutions" of a residue in a reference sequence are substitutions that are physically or functionally similar to the corresponding reference residue, e.g. that have a similar size, shape, electric charge, chemical properties, including the ability to form covalent or hydrogen bonds, or the like. Particularly preferred conservative substitutions are those fulfilling the criteria defined for an "accepted point mutation" as described by Dayhoff et al. ("Atlas of Protein Sequence and Structure", 1978, Nat. Biomed. Res. Foundation, Washington, D.C., Suppl. 3, 22: 354-352).

The terms "approximately" and "about", as used herein in reference to a number, generally include numbers that fall within a range of 10% in either direction of the number (greater than or less than the number) unless otherwise stated or otherwise evident from the context (e.g., where such number would exceed 100% of a possible value).

DETAILED DESCRIPTION OF CERTAIN PREFERRED EMBODIMENTS

As mentioned above, the present invention provides cyclic antimicrobial peptides that can be used in a variety of applications. In addition to strong antimicrobial properties, the cyclic antimicrobial peptides of the invention exhibit tremendous stability in human serum and are devoid of toxicity on human cells, in particular devoid of cytolytic activity on human cells.

I—Cyclic Antimicrobial Peptides

The present invention provides several cyclic antimicrobial peptides. As used herein, the term "cyclic peptide" refers to a polypeptide chain wherein the amino termini and carboxy termini are linked with a covalent bond thereby generating a ring. In order to indicate that the peptide is cyclic, the peptide sequence is provided between brackets.

As used herein, the term "antimicrobial peptide" refers to a peptide which prevents, inhibits or reduces the growth or function of a microorganism or which kills a microorganism, in particular a microorganism that is detrimental to mammal health, including human health. The antimicrobial activity can be determined by any conventional method known in the art. In certain preferred embodiments of the present invention, an antimicrobial peptide has antibacterial activity. As used herein, the term "antibacterial activity" refers to the ability to kill bacteria (bactericidal activity) or to prevent, inhibit or reduce bacterial growth or function (bacteriostatic activity).

More specifically, the cyclic antimicrobial peptides according to the present invention are derived from an SprA1 antimicrobial peptide. The term "SprA1 antimicrobial peptide" more specifically refers to an antimicrobial peptide that is produced by the gram-positive bacterium *Staphylococcus aureus*, and that is encoded by a small regulatory RNA located in a pathogenicity island of the *S. aureus* genome. The term "SprA1 antimicrobial peptide" also encompasses any antimicrobial peptide that can be derived from the SprA1-encoded antimicrobial peptide.

In particular, the present invention provides cyclic antimicrobial peptides having one of the following sequences:

```
(SEQ ID NO: 1, called Pep6 in the Examples)
(FFWLSRRTK), (SEQ ID NO: 2, called Pep7 in the Examples)
(FFWSRRTK), (SEQ ID NO: 3, called Pep8 in the Examples)
(FFWRRTK), (SEQ ID NO: 4, called Pep10 in the Examples)
(FFWLRR-ΨHyt-K), (SEQ ID NO: 5, called Pep11 in the Examples)
(FFWRR-ΨHyt-K), (SEQ ID NO: 6, called Pep12 in the Examples)
(Ψ1Nal-FWRR-ΨHyt-K), (SEQ ID NO: 7, called Pep13 in the Examples)
(FF-Ψ1Nal-WRR-ΨHyt-K), (SEQ ID NO: 8, called Pep14 in the Examples)
(Ψ2Nal-F-Ψ2Nal-RR-ΨHyt-K), (SEQ ID NO: 9, called Pep15 in the Examples)
(FF-Ψ2Nal-RR-ΨHyt-K), (SEQ ID NO: 10, called Pep16 in the Examples)
(Ψ2Nal-F-Ψ2Nal-RR-ΨV-K), (SEQ ID NO: 11, called Pep17 in the Examples)
(Ψ1Nal-F-Ψ1Nal-RR-ΨGlyco-K), (SEQ ID NO: 12, called Pep18 in the Examples)
(FFWRRVK), (SEQ ID NO: 13, called Pep19 in the Examples)
(Ψ1Nal-F-Ψ1Nal-RRVK), (SEQ ID NO: 14, called Pep20 in the Examples)
(ΨF-F-Ψ1Nal-RR-ΨHyt-K),
``` wherein

ΨHyt is aza-$\beta^3$-hydroxylthreonine

ΨV is aza-$\beta^3$-valine

ΨF is aza-$\beta^3$-phenylalanine

Ψ1Nal is aza-$\beta^3$-1-naphthylalanine

Ψ2Nal is aza-$\beta^3$-2-naphthylalanine

ΨGlyco is a glycol-amino acid having the following chemical structure (I):

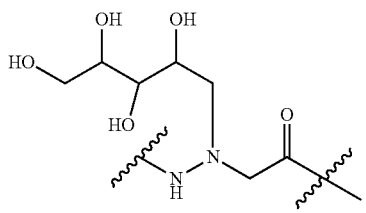

Preparation of the Cyclic Antimicrobial Peptides

The cyclic antimicrobial peptides according to the present invention may be prepared using any of a variety of suitable methods known in the art, such as for example by chemical synthesis.

For example, the cyclic antimicrobial peptides of the invention may be prepared using standard chemical methods. Solid-phase peptide synthesis, which was initially described by R. B. Merrifield (J. Am. Chem. Soc. 1963, 85: 2149-2154) is a quick and easy approach to synthesizing peptides and peptidic molecules of known sequences. A compilation of such solid-state techniques may be found, for example, in "Solid Phase Peptide Synthesis" (Methods in Enzymology, G. B. Fields (Ed.), 1997, Academic Press: San Diego, Calif., which is incorporated herein by reference in its entirety). Most of these synthetic procedures involve the sequential addition of one or more amino acid residues or suitable protected amino acid residues to a growing peptide chain. For example, the carboxy group of the first amino acid is attached to a solid support via a labile bond, and reacted with the second amino acid, whose amino group has, beforehand, been chemically protected to avoid self-condensation. After coupling, the amino acid group is deprotected, and the process is repeated with the following amino acid. Once the desired peptide is assembled, it is cleaved off from the solid support, precipitated, and the resulting free peptide may be analyzed and/or purified as desired. Solution methods, as described, for example, in "The Proteins" (Vol. II, $3^{rd}$ Ed., H. Neurath et al. (Eds.), 1976, Academic Press: New York, N.Y., pp. 105-237), may also be used to synthesize the cyclic antimicrobioal peptides of the invention. Cyclization methods are also known in the art (see, for example, Lambert et al., J. Chem. Soc., Perkin Trans, 1, 2001, 471-484).

Crude synthesized antimicrobial peptides may be purified using any suitable preparative technique such as reversed-phase chromatography, partition chromatography, gel filtration, gel electrophoresis, and ion-exchange chromatography.

II—Uses of the Cyclic Antimicrobial Peptides

Due to their biological activity, the cyclic antimicrobial peptides of the invention may be used in a variety of applications, including therapeutic applications. Indeed, the peptides disclosed have been found to exhibit antimicrobial activity against gram-positive and gram-negative bacteria. Detailed description of the microorganisms belonging to gram-positive and gram-negative bacteria can be found for example in "Medical Microbiology", $3^{rd}$ Ed., 1991, Churchill Livingstone, N.Y.).

Examples of gram-positive bacteria against which the cyclic antimicrobial peptides of the invention may be used include, but are not limited to, bacteria belonging to the *Staphylococcus, Micrococcus, Lactococcus, Lactobacillus, Clostridium, Bacillus, Streptococcus, Enterococcus*, or *Listeria* genus. In particular, the cyclic antimicrobial peptides of the invention may be used against gram-positive bacteria that are potentially pathogenic to humans or other mammals. Such gram-positive bacteria include, but are not limited to, *Staphylococcus aureus, Staphylococcus epidermidis, Staphylococcus saprophyticus, Staphylococcus hyicus, Staphylococcus intermedius, Clostridium tetani, Clostridium botulinum, Clostridium perfringens, Clostridium difficile, Bacillus cereus, Bacillus anthracis, Streptococcus pyogenes, Streptococcus agalactiae, Streptococcus pneumoniae, Enterococcus faecalis, Enterococcus faecium, Listeria monocytogenes*, and *Listeria ivanovii*.

Examples of gram-negative bacteria against which the cyclic antimicrobial peptides of the invention may be used include, but are not limited to, bacteria belonging to the *Bordetella, Salmonella, Enterobacter, Klebsiella, Shigella, Yersinia, Escherichia coli, Vibrio, Pseudomonas, Neisseria, Haemophilus*, or *Agrobacterium* genus. In particular, the cyclic antimicrobial peptides of the invention may be used against gram-negative bacteria that are potentially pathogenic to humans or other mammals. Such gram-negative bacteria include, but are not limited to, *Bordetella pertussis, Bordetella parapertussis, Bordetella bronchiseptica, Shigella boydii, Shigella dysenteriae, Shigella flexneri, Shigella sonnei, Enterobacter aerogenes, Enterobacter cloacae, Enterobacter sakozakii, Klebsiella pneumoniae, Yersinia pestis, Yersina enterocolitica, Yersina pseudotuberculosis, Salmonella enterica, Vibrio cholerae, Vibrio parahaemolyticus, Vibrio vulnificus, Vibrio fluvialis, Neisseria meningitidis, Neisseria gonorrhoeae, Haemophilus influenzae, Haemophilus aegypticus*, and *Haemophilus ducreyi*.

The antimicrobial peptides of the present invention are therefore useful as bactericides and/or bacteriostats for modification of infectivity, killing microorganisms, or inhibiting microbial growth or function, and thus are useful for the treatment of an infection or contamination caused by such microorganisms.

1—Therapeutic Applications

A. Indications

The present invention concerns both humans and other mammals such as horses, dogs, cats, cows, pigs, camels, among others, and is applicable in human medicine and veterinary therapy.

Thus, a cyclic antimicrobial peptide according to the present invention may be used for the treatment of any disease or condition caused by or due to a gram-positive or gram-negative bacterium. Bacterial infections include, but are not limited to, urinary infections, skin infections, intestinal infections, lung infections, ocular infections, otitis, sinusitis, pharyngitis, osteo-articular infections, genital infections, dental infections, oral infections, septicemia, nocosomial infections, bacterial meningitis, gastroenteritis, gastritis, diarrhea, ulcers, endocarditis, sexually transmitted diseases, tetanus, diphtheria, leprosy, cholera, listeriosis, tuberculosis, salmonellosis, dysentery, and the like. Bacterial diseases are contagious and can result in many serious or life-threatening complications, such as blood poisoning, kidney failure and toxic shock syndrome.

Methods of treatment of the present invention may be accomplished using an inventive cyclic antimicrobial peptide, or a pharmaceutical composition thereof. These methods generally comprise administering an effective amount of at least one cyclic antimicrobial peptide, or a pharmaceutical composition thereof, to a subject in need thereof. Administration may be performed using any of the methods known to one skilled in the art. In particular, a cyclic antimicrobial peptide or composition thereof may be administered by any of various routes including, but not limited to, aerosol, parenteral, oral or topical route.

In general, an inventive cyclic antimicrobial peptide or a composition thereof will be administered in an effective amount, i.e., an amount that is sufficient to fulfill its intended purpose. The exact amount of cyclic antimicrobial peptide, or pharmaceutical composition thereof, to be administered will vary from subject to subject, depending on the age, sex, weight and general health condition of the subject to be treated, the desired biological or medical response and the like. In certain embodiments, an effective amount is one that prevents bacterial infection. In other embodiments, an efficient amount is one that treats bacterial infection by killing microorganisms and/or by inhibiting bacterial growth or function. In most embodiments, an effective amount of a cyclic antimicrobial peptide, or of a pharmaceutical composition thereof, is one that results in treatment of the disorder for which it is administered, e.g. slowing down or stopping the progression, aggravation or deterioration of the symptoms of the disorder and/or bringing about amelioration of the symptoms of the disorder, and/or curing the disorder. The effects of a treatment according to the invention may be monitored using any of the assays known in the art for the diagnosis of the disease being treated.

In certain embodiments, an inventive cyclic antimicrobial peptide, or a composition thereof, is administered alone according to a method of treatment of the present invention. In other embodiments, an inventive cyclic antimicrobial peptide, or a composition thereof, is administered in combination with at least one additional therapeutic agent or therapeutic procedure. The cyclic antimicrobial peptide or composition may be administered prior to administration of the additional therapeutic agent or therapeutic procedure, concurrently with the therapeutic agent or procedure, and/or following administration of the additional therapeutic agent or procedure.

Therapeutic agents that may be administered in combination with an inventive cyclic antimicrobial peptide, or composition thereof, may be selected among a large variety of biologically active compounds including compounds that are known to have a beneficial effect in the treatment of the infection for which the cyclic antimicrobial peptide is administered; compounds that are known to be active against a condition or symptom associated with the infection treated; and compounds that increase the availability and/or activity of the cyclic antimicrobial peptide. Examples of such biologically active compounds include, but are not limited to, anti-inflammatory agents, immunomodulatory agents, analgesics, antimicrobial agents, antibacterial agents, antibiotics, antioxidants, antiseptic agents, and the like.

Therapeutic procedures that may be performed in combination with administration of an inventive cyclic antimicrobial peptide, or composition thereof, include, but are not limited to, surgery, catheterization and other invasive therapeutic procedures. Indeed, an inventive cyclic antimicrobial peptide may be used to prevent bacterial infection in association with urinary catheter use or use of central venous catheters. An inventive cyclic antimicrobial peptide, in plasters, adhesives, sutures or wound dressings, may also be used for prevention of infection post-surgery.

B. Administration

An inventive cyclic antimicrobial peptide (optionally after formulation with one or more appropriate pharmaceutically acceptable carriers or excipients), in a desired dosage can be administered to a subject in need thereof by any suitable route. Various delivery systems are known and can be used to administer cyclic antimicrobial peptides of the present invention, including tablets, capsules, injectable solutions, encapsulation in liposomes, microparticles, microcapsules, etc. Methods of administration include, but are not limited to, dermal, intradermal, intramuscular, intraperitoneal, intralesional, intravenous, subcutaneous, intranasal, pulmonary, epidural, ocular, and oral routes. An inventive cyclic antimicrobial peptide, or composition thereof, may be administered by any convenient or other appropriate route, for example, by infusion or bolus injection, by adsorption through epithelial or mucocutaneous linings (e.g., oral, mucosa, rectal and intestinal mucosa, etc). Administration can be systemic or local. Parenteral administration may be directed to a given tissue of the patient, such as by catheterization. As will be appreciated by those of ordinary skill in the art, in embodiments where an inventive cyclic antimicrobial peptide is administered along with an additional therapeutic agent, the cyclic antimicrobial peptide and therapeutic agent may be administered by the same route (e.g., orally) or by different routes (e.g., orally and intravenously).

As mentioned above, an inventive cyclic antimicrobial peptide (optionally after formulation with one or more appropriate pharmaceutically acceptable carriers or excipients) may alternatively be administered incorporated in, or coating, bandages, plasters, sutures, catheters, needles, adhesives, wound dressings or implants.

C. Dosage

Administration of an inventive cyclic antimicrobial peptide (or a composition thereof) of the present invention will be in a dosage such that the amount delivered is effective for the intended purpose. The route of administration, formulation and dosage administered will depend upon the therapeutic effect desired, the severity of the disease being treated, the age, sex, weight and general health condition of the patient as well as upon the potency, bioavailability and in vivo half-life of the cyclic antimicrobial peptide used, the use (or not) of concomitant therapies, and other clinical factors. These factors are readily determinable by the attending physician in the course of the therapy. Alternatively or additionally, the dosage to be administered can be determined from studies using animal models. Adjusting the dose to achieve maximal efficacy based on these or other methods are well known in the art and are within the capabilities of trained physicians. As studies are conducted using cyclic antimicrobial peptides of the invention, further information will emerge regarding the appropriate dosage levels and duration of treatment.

A treatment according to the present invention may consist of a single dose or multiple doses. Thus, administration of an inventive cyclic antimicrobial peptide, or composition thereof, may be constant for a certain period of time or periodic and at specific intervals, e.g., hourly, daily, weekly (or at some other multiple day interval), monthly, yearly (e.g., in a time release form). Alternatively, the delivery may occur at multiple times during a given time period, e.g., two or more times per week, two or more times per month, and the like. The delivery may be continuous delivery for a period of time, e.g., intravenous delivery.

2—Cleaning, Disinfection, Decontamination Applications

The cyclic antimicrobial peptides of the present invention may also be used in any application where the absence of bacterial contamination on inanimate (non-living) objects is desired. Examples of such inanimate objects include, but are not limited to, medical devices (e.g., instruments, apparatus, implants, contact lenses, laboratory coats, scrubs, gloves, and the like); surfaces floors, furniture, and the like) of operating rooms in hospitals, laboratories, industrial installations, public places or private housing.

Accordingly, the present invention provides for the use of an inventive cyclic antimicrobial peptide as disinfectant. The invention also provides a method for cleaning or disinfecting the surface of an object or for preventing bacterial contamination of the surface of an object comprising a step of contacting the surface of the object with an effective amount of an inventive cyclic antimicrobial peptide.

The cyclic antimicrobial peptide may be comprised in a cleaning solution or product. Accordingly, the present invention provides a cleaning solution or clearing product comprising at least one cyclic antimicrobial peptide as described herein. The cleaning product may be a cleaning pad or cleaning wipe.

Other examples of inanimate objects include products that come in contact with the human body including personal care products (e.g., soap, shampoos, tooth paste, deodorant, sunscreens, tampons, diapers, and the like) and cosmetics. The cyclic antimicrobial peptide may be comprised in the products or the products may be soaked, sprayed or coated with the cyclic antimicrobial peptide.

III—Products and Pharmaceutical Compositions

As mentioned above, in the therapeutic applications, the cyclic antimicrobial peptides of the invention, may be administered per se or as a pharmaceutical composition. Accordingly, the present invention provides pharmaceutical compositions comprising an effective amount of at least one cyclic antimicrobial peptide and at least one pharmaceutically acceptable carrier or excipient. In some embodiments, the composition further comprises one or more additional biologically active agents.

The cyclic antimicrobial peptides and pharmaceutical compositions thereof may be administered in any amount and using any route of administration effective for achieving the desired prophylactic and/or therapeutic effect. The optimal pharmaceutical formulation can be varied depending upon the route of administration and desired dosage. Such formulations may influence the physical state, stability, rate of in vivo release, and rate of in vivo clearance of the administered active ingredient.

The pharmaceutical compositions of the present invention may be formulated in dosage unit form for ease of administration and uniformity of dosage. The expression "unit dosage form", as used herein, refers to a physically discrete unit of a cyclic antimicrobial peptide for the patient to be treated. It will be understood, however, that the total daily dosage of the compositions will be decided by the attending physician within the scope of sound medical judgement.

A. Formulation

Injectable preparations, for example, sterile injectable aqueous or oleaginous suspensions may be formulated according to the known art using suitable dispersing or wetting agents, and suspending agents. The sterile injectable preparation may also be a sterile injectable solution, suspension or emulsion in a non-toxic parenterally acceptable diluent or solvent, for example, as a solution in 2,3-butanediol. Among the acceptable vehicles and solvents that may be employed are water, Ringer's solution, U.S.P. and isotonic sodium chloride solution. In addition, sterile, fixed oils are conventionally employed as a solution or suspending medium. For this purpose any bland fixed oil can be employed including synthetic mono- or di-glycerides. Fatty acids such as oleic acid may also be used in the preparation of injectable formulations. Sterile liquid carriers are useful in sterile liquid form compositions for parenteral administration.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use. Liquid pharmaceutical compositions which are sterile solutions or suspensions can be administered by, for example, intravenous, intramuscular, intraperitoneal or subcutaneous injection. Injection may be via single push or by gradual infusion. Where necessary or desired, the composition may include a local anesthetic to ease pain at the site of injection.

In order to prolong the effect of an active ingredient, it is often desirable to slow the absorption of the ingredient from subcutaneous or intramuscular injection. Delaying absorption of a parenterally administered active ingredient may be accomplished by dissolving or suspending the ingredient in an oil vehicle. Injectable depot forms are made by forming micro-encapsulated matrices of the active ingredient in biodegradable polymers such as polylactide-polyglycolide. Depending upon the ratio of active ingredient to polymer and the nature of the particular polymer employed, the rate of ingredient release can be controlled. Examples of other biodegradable polymers include poly(orthoesters) and poly(anhydrides). Depot injectable formulations can also be prepared by entrapping the active ingredient in liposomes or microemulsions which are compatible with body tissues.

Liquid dosage forms for oral administration include, but are not limited to, pharmaceutically acceptable emulsions, microemulsions, solutions, suspensions, syrups, elixirs, and pressurized compositions. In addition to the cyclic antimicrobial peptide, the liquid dosage form may contain inert diluents commonly used in the art such as, for example, water or other solvent, solubilising agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cotton seed, ground nut, corn, germ, olive, castor, and sesame oils), glycerol, tetrahydrofurfuryl alcohol, polyethylene glycols, and fatty acid esters of sorbitan and mixtures thereof. Besides inert diluents, the oral compositions can also include adjuvants such as wetting agents, suspending agents, preservatives, sweetening, flavouring, and perfuming agents, thickening agents, colors, viscosity regulators, stabilizes or osmo-regulators. Examples of suitable liquid carriers for oral administration include water (potentially containing additives as above, e.g., cellulose derivatives, such as sodium carboxymethyl cellulose solution), alcohols (including monohydric alcohols and polyhydric alcohols such as glycols) and their derivatives, and oils (e.g., fractionated coconut oil and arachis oil). For pressurized compositions, the liquid carrier can be halogenated hydrocarbon or other pharmaceutically acceptable propellant.

Solid dosage forms for oral administration include, for example, capsules, tablets, pills, powders, and granules. In such solid dosage forms, an inventive cyclic antimicrobial peptide may be mixed with at least one inert, pharmaceutically acceptable excipient or carrier such as sodium citrate or dicalcium phosphate and one or more of: (a) fillers or extenders such as starches, lactose, sucrose, glucose, mannitol, and silicic acid; (b) binders such as, for example, carboxymethylcellulose, alginates, gelatine, polyvinylpyrrolidone, sucrose, and acacia; (c) humectants such as glycerol; (d) disintegrating agents such as agar-agar, calcium carbonate, potato or tapioca starch, alginic acid, certain silicates, and sodium carbonate; (e) solution retarding agents such as paraffin; absorption accelerators such as quaternary ammonium compounds; (g) wetting agents such as, for example, cetyl alcohol and glycerol monostearate; (h) absorbents such as kaolin and bentonite clay; and (i) lubricants such as talc, calcium stearate, magnesium stearate, solid polyethylene glycols, sodium lauryl sulphate, and mixtures thereof. Other excipients suitable for solid formulations include surface modifying agents such as non-ionic and anionic surface modifying agents. Representative examples of surface modifying agents include, but are not limited to, poloxamer 188, benzalkonium chloride, calcium stearate, cetostearyl alcohol, cetomacrogol emulsifying wax, sorbitan esters, colloidal silicon dioxide, phosphates, sodium dodecylsulfate, magnesium aluminum silicate, and triethanolamine. In the case of capsules, tablets and pills, the dosage form may also comprise buffering agents.

Solid compositions of a similar type may also be employed as fillers in soft and hard-filled gelatine capsules using such excipients as lactose or milk sugar as well as high molecular weight polyethylene glycols and the like. The solid dosage forms of tablets, dragees, capsules, pills, and granules can be prepared with coatings and shells such as enteric coatings, release controlling coatings and other coatings well known in the pharmaceutical formulating art. They may optionally contain opacifying agents and can also be of a composition such that they release the active ingredient(s) only, or preferably, in a certain part of the intestinal tract, optionally, in a delaying manner. Examples of embedding compositions which can be used include polymeric substances and waxes.

In certain embodiments, it may be desirable to administer an inventive composition locally to an area in need of treatment. This may be achieved, for example, and not by way of limitation, by local infusion during surgery, topical application, by injection, by means of a catheter, by means of suppository, or by means of a skin patch or stent or other implant.

For topical administration, the composition is preferably formulated as a gel, an ointment, a lotion, or a cream which can include carriers such as water, glycerol, alcohol, propylene glycol, fatty alcohols, triglycerides, fatty acid esters, or mineral oil. Other topical carriers include liquid petroleum, isopropyl palmitate, polyethylene glycol, ethanol (95%), polyoxyethylenemonolaurat (5%) in water, or sodium lauryl sulphate (5%) in water. Other materials such as antioxidants, humectants, viscosity stabilizers, and similar agents may be added as necessary.

In addition, in certain instances, it is expected that the inventive compositions may be disposed within transdermal devices placed upon, in, or under the skin. Such devices include patches, implants, and injections which release the active ingredient by either passive or active release mechanisms. Transdermal administrations include all administration across the surface of the body and the inner linings of bodily passage including epithelial and mucosal tissues. Such administrations may be carried out using the present compositions in lotions, creams, foams, patches, suspensions, solutions, and suppositories (rectal and vaginal).

Transdermal administration may be accomplished through the use of a transdermal patch containing an active ingredient (i.e., the cyclic antimicrobial peptide) and a carrier that is non-toxic to the skin, and allows the delivery of the ingredient for systemic absorption into the bloodstream via the skin. The carrier may take any number of forms such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may be suitable. A variety of occlusive devices may be used to release the active ingredient into the bloodstream such as a semi-permeable membrane covering a reservoir containing the active ingredient with or without a carrier, or a matrix containing the active ingredient.

Suppository formulations may be made from traditional materials, including cocoa butter, with or without the addition of waxes to alter the suppository's melting point, and glycerine. Water soluble suppository bases, such as polyethylene glycols of various molecular weights, may also be used.

Materials and methods for producing various formulations are known in the art and may be adapted for practicing the subject invention. Suitable formulations for the delivery of antibodies can be found, for example, in "*Remington's Pharmaceutical Sciences*", E. W. Martin, 18$^{th}$ Ed., 1990. Mack Publishing Co.: Easton, Pa.

B. Additional Biologically Active Agents

In certain embodiments, an inventive cyclic antimicrobial peptide is the only active ingredient in a pharmaceutical composition of the present invention. In other embodiments, the pharmaceutical composition further comprises one or more biologically active agents. Examples of suitable biologically active agents include, but are not limited to, anti-inflammatory agents, immunomodulatory agents, analgesics, antimicrobial agents, antibacterial agents, antibiotics, antioxidants, antiseptic agents, and combinations thereof.

In such pharmaceutical compositions, the cyclic antimicrobial peptide and the at least one additional therapeutic agent may be combined in one or more preparations for simultaneous, separate or sequential administration of the cyclic antimicrobial peptide and therapeutic agent(s). More specifically, an inventive composition may be formulated in such a way that the cyclic antimicrobial peptide and therapeutic agent(s) can be administered together or independently from each other. For example, the cyclic antimicrobial peptide and therapeutic agent can be formulated together in a single composition. Alternatively, they may be maintained (e.g., in different compositions and/or containers) and administered separately.

C. Products Comprising an Inventive Cyclic Antimicrobial Peptide

The invention also relates to a product comprising an inventive cyclic antimicrobial peptide, or a pharmaceutical composition thereof, as defined above. The product may be selected from bandages, plasters, sutures, adhesives, wound dressings, implants, contact lenses, cleaning solutions, storage solutions (e.g., for contact lenses or medical devices), cleaning products (e.g., cleaning pads or wipes), personal care products (e.g., soap, shampoos, tooth paste, sunscreens, tampons, diapers, and the like), and cosmetics.

The products comprising an inventive cyclic antimicrobial peptide may be prepared by any suitable method. Generally, the method of preparation will depend on the nature of the object. For example, an inventive cyclic antimicrobial peptide, or a pharmaceutical composition thereof, may be added to the product by mixing, or may be incorporated or applied to a product by soaking the product into a solution of the cyclic antimicrobial peptide, by coating the product with the cyclic antimicrobial peptide, or by spraying the product with a solution of the cyclic antimicrobial peptide.

D. Pharmaceutical Packs or Kits

In another aspect, the present invention provides a pharmaceutical pack or kit comprising one or more containers (e.g., vials, ampoules, test tubes, flasks or bottles) containing one or more ingredients of an inventive pharmaceutical composition, allowing administration of a cyclic antimicrobial peptide of the present invention.

Different ingredients of a pharmaceutical pack or kit may be supplied in a solid (e.g., lyophilized) or liquid form. Each ingredient will generally be suitable as aliquoted in its respective container or provided in a concentrated form. Packs or kits according to the invention may include media for the reconstitution of lyophilized ingredients. Individual containers of the kits will preferably be maintained in close confinement for commercial sale.

In certain embodiments, a pack or kit includes one or more additional therapeutic agent(s). Optionally associated with the container(s) can be a notice or package insert in the form prescribed by a governmental agency regulating the manufacture, use or sale of pharmaceutical or biological products, which notice reflects approval by the agency of manufacture, use or sale for human administration. The notice of package insert may contain instructions for use of a pharmaceutical composition according to methods of treatment disclosed herein.

An identifier, e.g., a bar code, radio frequency, ID tags, etc., may be present in or on the kit. The identifier can be used, for example, to uniquely identify the kit for purposes of quality control, inventory control, tracking movement between workstations, etc.

EXAMPLES

The following examples describe some of the preferred modes of making and practicing the present invention. However, it should be understood that the examples are for illustrative purposes only and are not meant to limit the scope of the invention. Furthermore, unless the description in an Example is presented in the past tense, the text, like the rest of the specification, is not intended to suggest that experiments were actually performed or data were actually obtained.

Some of the results presented below have been described in a manuscript (Solecki et al., "Converting a *Staphylococcus aureus* Toxin into Effective Cyclic Pseudopeptide Antibiotics", which is to be submitted for publication in the journal Chemistry and Biology in October 2014. The entire content of the scientific paper is incorporated herein by reference in its entirety.

Materials and Methods

Chemicals.

Fmoc-protected amino acids were from Novabiochem and Iris Biotech (Marktredwitz, Germany). H-Rink amide ChemMatrix resin was from Sigma-Aldrich, TBTU was from Iris Biotech. Solvents for peptide synthesis and HPLC were from Carlo Erba-SdS (Sabadell, Spain). TFA was from Fluorochem Ltd (Derbyshire, UK). All other chemicals were purchased from Sigma-Aldrich at the highest quality available. Pep C-ter was from Proteogenix.

Automated Solid-Phase Synthesis.

Synthesis of linear peptides and pseudopeptides was accomplished using $N^\alpha$-Fmoc-amino acids, $N^\beta$-Fmoc-aza-$\beta^3$-amino acids, (Laurencin et al., J Med Chem., 2012, 55(24): 10885-10895) and a Rink Amide resin (100-200 mesh; 0.79 mmol/g) except for the native peptide PepA1, for which that a H-Rink amide Chem Matrix resin was used (0.5 mmol/g). Peptides were synthesized at 100 μmol scale. Peptides were assembled on the resin by automated Fmoc synthesis protocols run on a Liberty-12-channel synthesizer (CEM μWaves). Briefly, Fmoc groups were removed with piperidine/DMF (20%) using a short cycle (40 W, 75° C. 60 s) followed by a long cycle (40 W, 75° C., 180 s). After DMF washings, coupling was carried out with a 0.2 M solution of Fmoc-amino acid, in the presence of 0.5 M TBTU and 2 M DIPEA at 30 W, 68° C. for 5 minutes. Fmoc-Arg(Pbf) required an additional coupling step consisting of a long cycle at 0 W, 25° C. for 25 minutes followed by one short cycle at 30 W, 68° C. for 5 minutes. For Fmoc-His(Trt), deprotection was at 50° C. to avoid racemization, and a specific coupling cycle, again to avoid racemization, was used, consisting of an initial step at 0 W, 50° C. for 2 minutes followed by another at 30 W, 50° C. for 4 minutes. After synthesis completion, the N-deblocked peptide resins were side-chain deprotected and cleaved from the resin using TFA/H$_2$O/TIS (95:2.5:2.5, 3 h) with mild orbital shaking. After filtration of the mixtures the peptides were precipitated by addition of chilled diethyl ether, centrifuged at 4° C. (3000 g; 10 min) and the supernatants were discarded.

Peptides were analyzed by RP-HPLC on a XTerra C$_{18}$ column (4.6×100 mm, 3.5 μm) in a Waters 2696 system equipped with a 600 PDA and Empower software. Solvents A and B were 0.1% and 0.08% (v/v) TFA in H$_2$O and MeCN, respectively. Linear 5-60% gradients of B into A over 40 minutes and 60-95% B into A in 10 minutes were used for elution at 1 mL/min flow rate were used for elution, with UV detection at 215 nm. Preparative RP-HPLC was done on a XTerra C$_{18}$ column (19×300 mm, 10 μm, Waters) in a Waters 600 system. Solvents A and B were 0.1% TFA (v/v) in H$_2$O and 0.08% TFA (v/v) in MeCN, respectively. Linear 5-60% gradients of B into A over 40 minutes and 60-95% B into A in 10 minutes were used for elution, at 10 mL/min flow rate, with UV detection at 215 nm. Due to the hydrophobicity of PepA1 and the Pep N-ter, methanol was used instead of the acetonitrile in the same conditions. The homogeneity and identity of synthetic peptides were assessed by analytical C$_{18}$ reversed-phase HPLC. Peptides were satisfactorily checked for identity by mass spectrometry on MALDI-TOF (matrix-assisted laser-desorption ionization-time-of-flight) Daltonics microflex LT (Bruker).

H-MLIFVHIIAPVISGCAIAFFSYWLSRRNTK-NH$_2$ (PepA1-SEQ ID NO: 15): Yield after purification 4%; white powder; RP-HPLC R$_t$: 40.6 min; MALDI-TOF MS mass: m/z found 3452.80 [M+H$^+$]; calc.: 3452.88 [M+H$^+$].

H-MLIFVHIIAPVISGCAIA-NH$_2$ (Pep N-Ter-SEQ ID NO: 16): Yield after purification %; white powder; RP-HPLC R$_t$: 30.5 min; MALDI-TOF MS mass: m/z found 1867.32 [M+H$^+$]; calc.: 1867.06 [M+H$^+$].

H-FFSYWLSRRNTK-NH$_2$ (Pep1-SEQ ID NO: 17): Yield after purification 45%; white powder; RP-HPLC R$_t$: 26.8 min; MALDI-TOF MS mass: m/z found 1603.74 [M+H$^+$]; calc.: 1603.85 [M+H$^+$].

H-FFSYWLSRRTK-NH$_2$ (Pep2-SEQ ID NO: 18): Yield after purification 32%; white powder; RP-HPLC R$_t$: 30.5 min; MALDI-TOF MS mass: m/z found 1489.98 [M+H$^+$]; calc.: 1489.81 [M+H$^+$].

H-FFSWLSRRTK-NH$_2$ (Pep3-SEQ ID NO: 19): Yield after purification 41%; white powder; RP-HPLC R$_t$: 21.6 min; MALDI-TOF MS mass: m/z found 1326.74 [M+H$^+$]; calc.: 1326.74 [M+H$^+$].

H-FFWLSRRTK-NH$_2$ (Pep4-SEQ ID NO: 20): Yield after purification 31%; white powder; RP-HPLC R$_t$: 24.8 min; MALDI-TOF MS mass: m/z found 1239.70 [M+H$^+$]; calc.: 1239.71 [M+H$^+$].

H-FFWLSRTK-NH$_2$ (Pep5-SEQ ID NO: 21): Yield after purification 58%; white powder; RP-HPLC R$_t$: 30.5 20.8 min; MALDI-TOF MS mass: m/z found 1089.60 [M+H$^+$]; calc.: 1089.61 [M+H$^+$].

H-FFWLRRΨHytK-NH$_2$ (Pep9-SEQ ID NO: 22): Yield after purification 28%; white powder; RP-HPLC R$_t$: 18 min; MALDI-TOF MS mass: m/z found 1197.79 [M+H$^+$]; calc.: 1197.70 [M+H$^+$].

For cyclic peptides, a 2-chlorotrityl chloride (CTC) resin was used. Typically, 2-chlorotrityl chloride resin (100-200 mesh; 1.2 mmol/g, 1 g) was swelled in dry dichloromethane (DCM) (10 mL) for 10 minutes. The first monomer was attached onto the resin by adding a solution of Nα-Fmoc-amino acid (1.2 equiv) in dry DCM (10 mL) and DIPEA (4 equiv) with mild orbital shaking for 4 hours at room temperature under nitrogen. The loading resin was washed with dimethylformamide (DMF) (5×10 mL), dry DCM (3×10 mL), and then with a mixture of DCM/MeOH/DIPEA (17/2/1) (2×10 mL), and finally with DMF (3×10 mL). The yield of the loading step was determined on the absorption of dibenzofulvene-piperidine adduct (λmax=301 nm). Cyclic peptides were synthesized with the same protocol as described previously. At the end of the synthesis, the resin was washed with DCM, dried, and then treated with a solution of 3% TFA in DCM (30 mL) for 20 minutes at room temperature. The resin slurries were then filtered. The cleavage solution was neutralized with a solution of N-methyl morpholine and the resulting solution was diluted in DCM (170 mL). The linear peptides were slowly added to a solution of EDC, HOBt (4 equiv), and DIEA (4 equiv) in DCM (to a final concentration of $10^{-4}$ M). The resulting mixture was stirred for 2 days. The crude mixture was partially concentrated in vacuo (100 mL). The resulting solution was washed with 0.5 M HCl, water, and saturated sodium chloride. The organic phases were dried under sodium sulfate then concentrated. Side chain deprotection with a solution of 10 mL of TFA/H$_2$O/TIS (95:2.5:2.5, 3 h), purification and characterisation of peptides were performed with the same as described previously.

(FFWLSRRTK) (Pep6-SEQ ID NO: 1): Yield after purification 3%; white powder; RP-HPLC R$_t$: 33.0 min; MALDI-TOF MS mass: m/z found 1229.69 [M+H$^+$]; calc.: 1229.69 [M+H$^+$].

(FFWSRRTK) (Pep7-SEQ ID NO: 2): Yield after purification 12%; white powder; RP-HPLC R$_t$: 26.8 min; MALDI-TOF MS mass: m/z found 1110.92 [M+H$^+$]; calc.: 1110.92 [M+H$^+$].

(FFWRRTK) (Pep8-SEQ ID NO: 3): Yield after purification 8%; white powder; RP-HPLC R$_t$: 26.8 min; MALDI-TOF MS mass: m/z found 1110.92 [M+H$^+$]; calc.: 1110.92 [M+H$^+$].

(FFWLRRΨHytK) (Pep10-SEQ ID NO: 4): Yield after purification 6%; white powder; RP-HPLC R$_t$: 29.2 min; MALDI-TOF MS mass: m/z found 1180.67 [M+H$^+$]; calc.: 1180.67 [M+H$^+$].

(FFWRRΨHytK) (Pep11-SEQ ID NO: 5): Yield after purification 16%; white powder; RP-HPLC R$_t$: 26.8 min; MALDI-TOF MS mass: m/z found 1067.35 [M+H$^+$]; calc.: 1067.59 [M+H$^+$].

(Ψ1Nal-FWRR-ΨHyt-K) (Pep12-SEQ ID NO: 6): Yield after purification 22%; white powder; RP-HPLC R$_t$: 22.1 min; MALDI-TOF MS mass: m/z found 1155.62 [M+Na$^+$]; calc.: 1132.62 [M+H$^+$].

(FF-Ψ1Nal-WRR-ΨHyt-K) (Pep13-SEQ ID NO: 7): Yield after purification 25%; white powder; RP-HPLC R$_t$: 21.9 min; MALDI-TOF MS mass: m/z found 1093.60 [M+H$^+$]; calc.: 1093.61[M+H$^+$].

(Ψ2Nal-F-Ψ2Nal-RR-ΨHyt-K) (Pep14-SEQ ID NO: 8): Yield after purification 18%, white powder; RP-HPLC R$_t$: 26.2 min; MALDI-TOF MS mass: m/z found 1156.46 [M+Na$^+$]; calc.: 1143.62[M+H$^+$].

(FFΨ2-Nal-RR-ΨHyt-K) (Pep15-SEQ ID NO: 9): Yield after purification 17%; white powder; RP-HPLC R$_t$: 26.2 min; MALDI-TOF MS mass: m/z found 1093.52 [M+H$^+$]; calc.: 1093.61[M+H$^+$].

(Ψ2Nal-F-Ψ2Nal-RR-ΨV-K) (Pep16-SEQ ID NO: 10): Yield after purification 21%; white powder; RP-HPLC R$_t$: 27.2 min; MALDI-TOF MS mass: m/z found 1226.69 [M+H$^+$]; calc.: 1226.64 [M+H$^+$].

(Ψ1Nal-F-Ψ1Nal-RR-ΨGlyco-K) (Pep17-SEQ ID NO: 11): Yield after purification 7%; white powder; RP-HPLC R$_t$: 22.8 min; MALDI-TOF MS mass: m/z found 1234.79 [M+Na$^+$+K$^+$]; calc.: 1173.67 [M+H$^+$].

(FFWRRVK) (Pep18-SEQ ID NO: 12): Yield after purification 11%; white powder; RP-HPLC R$_t$: 23.3 min; MALDI-TOF MS mass: m/z found 1020.62 [M+H$^+$]; calc.: 1020.60 [M+H$^+$].

(Ψ1Nal-F-Ψ1Nal-RRVK) (Pep19-SEQ ID NO: 13): Yield after purification 17%; white powder; RP-HPLC R$_t$: 26.5 min; MALDI-TOF MS mass: m/z found 1111.83 [M+H$^+$]; calc.: 1111.63[M+H$^+$].

(ΨF-F-Ψ1Nal-RR-ΨHyt-K) (Pep20-SEQ NO: 14): Yield after purification 27%; white powder; RP-HPLC R$_t$: 23.6 min; MALDI-TOF MS mass: m/z found 1108.81 [M+H$^+$]; calc.: 1108.62[M+H$^+$].

H-Ψ2Nal-F-Ψ2Nal-RR-ΨV-K-NH$_2$ (Pep21-SEQ ID NO: 23): Yield after purification 38%; white powder; RP-HPLC R$_t$: 25.6 min; MALDI-TOF MS mass: m/z found 1015.65 [M+H$^+$]; calc.: 1015.61[M+H$^+$].

Peptides stability in human sera. The stability of Nisin, Melittin and synthetic peptides were tested in vitro, as described (Laurencin et al., J Med Chem., 2012, 55(24): 10885-10895). Typically, 1.35 mL of 25% Human serum in a 1.5 mL Eppendorf tube was preincubated at 37±1° C. for 15 minutes prior to addition of 150 μL of peptide or pseudopeptide stock solution (10-2 M in water) to make the final peptide concentration 10-4 mmol/mL. The initial time was recorded, and at known time intervals, 100 μL of reaction solution was removed and quenched by adding 200 μL of 95% EtOH and adjusted at pH=2 to eliminate the effect of peptides adsorption to the protein of the human serum. The cloudy reaction sample was cooled (4° C.) for 15 minutes and then spun at 14 000 rpm (Eppendorf centrifuge) for 4 minutes to pellet the precipitated serum proteins. After centrifugation, the supernatants were collected, evaporated, and diluted in 100 μL of H$_2$O and then analyzed by RP-HPLC on a C18 XTerra (4.6 mm×250 mm, 5 μm) column using water-0.08% TFA (A)/acetonitrile-1% TFA (B) linear gradient (5-95% B in 45 min, 1 ml/min, 25° C., 214 nm and 280 nm). For melittin, nisin and synthetic peptides, HPLC peak areas were used to calculate the percentage of intact compound remaining at the various time points during the incubation.

Antibacterial Assays.

The antibacterial activity of the synthesized peptides was measured using a standard microdilution assay. Two bacterial species were tested, *Staphylococcus aureus* strain Newman and *Escherichia coli* strain K12 XL-Blue. Bacterial strains were subcultured in Mueller-Hinton broth. It was checked that both strains grown with the same efficiency in the same physical conditions in this medium. Bacteria were grown to an optical density (600 nm) of 0.5 and diluted $10^3$ times in MH broth. Cell density in wells was $10^5$ cfu/mL. 100 μL of this suspension was mixed with 100 μL of 2-fold serial dilutions of peptides in the well of a microtitre plate. Purified peptides were first dissolved in appropriate solvent to a final concentration of 2 mg/mL, in the microtitre plate, dilutions were made in MH broth from 1 to 0.004 mg/mL. MIC defined as the lowest concentration of purified peptide that inhibited growth, was determined after 20 hours incubation at 37° C. in a BioTek Plate Reader. Nisin (nisin from Lactococcus lactis, Sigma-Aldrich) was also tested on bacterial strains for reference. For tests against *E. coli*, EDTA was added to nisin to a final concentration of 20 mM. To determine minimum bactericidal concentration, bacterial suspensions in wells around MIC were plated out on BHI agar and incubated 24 hours at 37° C. The peptide concentration at which no colonies were observed was defined as the MBC. Results obtained in massic concentrations were converted to molar concentrations for proper comparisons. Tests were performed in triplicate.

Lytic Activity Against Human Erythrocytes.

Human blood was collected from EFS ('Etablissement Francais du Sang') in Rennes (France). Red blood cells (RBC) were recovered to a final concentration of 3% in PBS buffer. 100 µL of this suspension was mixed with 100 µL of 2-fold serial dilutions of purified peptide in microtiter plate with v-bottom, from 1 to 0.004 mg/mL in PBS buffer. The plates were incubated 2 hours at 37° C. After centrifugation, the absorbance of the supernatant was measured at 414 nm. Three wells were positive controls, where the RBC were mixed with water 1% Triton X-100, in these wells the totality of RBC were hemolyzed and the release of hemoglobin was considered to be 100%. Three wells were negative controls, where the RBC were mixed with PBS buffer, in these wells hemolysis was considered to be null. The percentage of hemolysis in each test well was calculated by comparing with controls. For each peptide, bloods from three different donors were tested.

Permeabilization Assays.

*E. coli* outer and inner membrane permeability was determined by using *E. coli* strain ML-35p, which is lactose permease deficient. Nitrocefin, β-lactam is excluded by the outer cell membrane but, if it can pass this barrier thanks to the action of an AMP, it is then cleaved by the β-lactamase localized within the periplasm. ONPG, passes through lac permease and is cleaved by the cytoplasmic β-galactosidase, however with the ML-35p *E. coli* strain, ONPG is excluded unless permeabilization is achieved. The permeabilization assays were carried out with 100 µL of bacteria in MH broth at $A_{600\ nm}$ 0.1-0.2 ($10^7$ cfu/mL, density necessary to detect degradation products). Following addition of the tests molecules at concentrations of 6 µM and 12 µM against $10^5$ cfu/mL (sub-MIC and supra-MIC respectively), nitrocefin (20 µg/mL final concentration) cleavage was monitored by light absorption measurements at 500 nm. ONPG was added to a 100 µg/ml final concentration and substrate cleavage was monitored by light absorption measurements at 420 nm. Polymixin B at 8 µM against $10^7$ cfu/mL was used as positive control. Bacterial suspension in MH broth plus substrates was used as negative control (untreated cells).

Scanning Electron Microscopy (SEM).

Bacterial strains were cultured in MH broth to an optical density (600 nm) of 0.5 corresponding to $10^8$ cfu/mL, a bacterial density necessary for SEM analysis. Red blood cells were recovered to a final concentration of 3% in PBS buffer the same used in hemolytic assays, a density sufficient for SEM analysis. Following addition of peptides, PepA1 and Pep11, samples were left 2 hours at room temperature before centrifugation for SEM preparation. Preliminary assays were performed with nisin against *S. aureus*, different concentrations i.e. 3, 6, 10, 30 and 100 µM against $10^5$ cfu/mL were tested. Only the slight sub-MIC concentration of 6 µM allowed obtaining suitable images on the effect on membrane. With the 3 µM concentration, effects could be observed but were rare and with increase concentrations, elevated bursted cells were observed. Therefore, the inventors chose to expose the two bacterial species to slight sub-MIC concentrations i.e. 6 µM for PepA1 against both bacterial species and 6 µM and 2 µM for Pep11 against *S. aureus* and *E. coli* respectively. Concerning RBC, the inventors knew that no hemolysis occurred at MIC for Pep11, therefore concentrations used against bacteria were not adapted to observe membrane effect on RBC. They also wanted to compare both peptides by using the same concentration of 0.2 mg/mL at which 50% hemolysis for PepA1 was expected and 10% for Pep11. This corresponds to 50 µM and 160 µM for PepA1 and Pep11 respectively. Preparations for SEM examination were obtained after centrifugation of cell suspensions (1000-3000 g during 5 minutes). Samples were fixed for 4 hours or 20 hours for RBC or bacteria respectively with 2.5% glutaraldehyde in 0.1 M cacodylate buffer, pH 7.2, rinsed then post fixed for 2 hours with 1% $OsO_4$ in the same buffer and eventually washed. Samples were carefully embedded in agar 2% then dehydrated in a graded series of increasing concentrations of ethanol (50, 70, 90 and 100% v/v). For SEM observation, samples were obtained after preparation with a Leica EM CPD 300 to reach drying in the critical point. Samples were metalized with gold palladium during 30 seconds (few nanometers on the surface) in a Leica EM ACE 200. The observation of the samples was performed using a SEM JEOL JSM 6301F at 7 kV with a work distance of 15 mm.

Results

When its expression is stimulated into the bacterial cytoplasm, the PepA1 peptide accumulates into the *S. aureus* membranes and destroys these membranes (Sayed et al., J. Biol. Chem., 2012, 287: 43454-43463). Interestingly, the present Inventors have found that synthesized PepA1 exhibits its antibacterial activity against Gram-positive (*S. aureus*) and Gram-negative (*E. Coli*) bacteria, possessing an 8 µM Minimal Inhibitory Concentration (MIC, Table 1) and a 16 µM Minimum Bactericidal Concentration (MBC) against these two bacteria. Hemolytic activity against human erythrocytes, however, was also detected and was found to correspond to 20% of hemolysis at the MIC.

The N-terminal (Pep N-ter) and the C-terminal (Pep C-ter) domains of PepA1 were chemically synthesized and their antibacterial activities tested. Pep N-ter was found to exhibit no detectable activity against the two bacterial species up to a 620 µM concentration, although 20% hemolysis was detected at that concentration (Table 1). Pep C-ter, however, was found to exhibit low antibacterial activity (a 15-fold higher MIC than that of Nisin and PepA1) and 20% hemolysis was detected at the MIC (150 µM). The deletion of the three amino acids (AIA) at the N-terminal led to the 12-mer peptide, Pep1, which was found to have a similar MIC-value than Pep C-ter. The deletion of residues AIA, interestingly, considerably reduced Pep1 hemolytic activity (about 7% at the highest tested concentration of 1 mg/mL, about 620 µM and 0.5% hemolysis at the MIC of ~155 µM). Pep1 MIC against *S. aureus* and *E. coli*, however, remained high, about 16 times higher than that of Nisin, a reference antibacterial peptide with 34 amino acid residues used as a food preservative.

Different chemical modifications (amino acid deletions, cyclization, introduction of modified, unatural amino acid, etc . . . ) were performed on Pep1 and the antibacterial properties and toxicity against human erythrocytes were assessed (see Table 1 and Table 2).

Pep2 was found to present hemolytic and antimicrobial activities similar to Pep1. Peptides Pep1 to Pep4 possess similar activities. Pep5 antibacterial effectiveness was found to be low, with a MIC against *S. aureus* and *E. coli* two-fold higher than Pep4. Therefore, Pep4 was retained as the minimal sequence retaining antibacterial activity but no hemolytic side effects. Remarkably and compared to Pep5, Pep6 (which corresponds to Pep4 after cyclization) MIC against *S. aureus* and *E. coli* bacteria were reduced ten-fold, unfortunately accompanied with substantial hemolysis against human erythrocytes. Pep7 is one residue-shorter compared to Pep6 and lacks a leucine hydrophobic residue that slightly reduces its hemolytic activity while increasing two-fold its antibacterial activity. Compared to Pep7, Pep8 is shorter, missing a serine residue. Pep8 was found to be 10-fold less hemolytic and ~3-fold more antibacterial than Pep7. Pep8 cyclic heptapeptide was found to be the most active peptide that contains all natural, unmodified, amino acids. Cyclic Pep6 has a 4-fold higher activity than linear Pep4 (identical sequences between Pep4 and Pep6), and this increased antimicrobial activity associated to cyclization was also detected for cyclic Pep10 versus linear Pep9 (identical sequences between Pep9 and Pep10).

TABLE 1

Antibacterial activity against Gram-negative and Gram-positive bacteria and toxicity against human erythrocytes of PepA1 and a series of short, linear, cyclic or hybrid pseudopeptide derivatives.

| Peptides | Human cells $H_{50}$ (μM) | *S. aureus* MIC (μM) | *S. aureus* TI $H_{50}$/MIC | *E. coli* MIC (μM) | *E. coli* TI $H_{50}$/MIC |
|---|---|---|---|---|---|
| PepA1 | 70 | 8 | 9 | 8 | 9 |
| Pep N-ter | nd | nd | | nd | nd |
| Pep C-ter | 420 | 150 | 3 | 75 | 6 |
| Pep1 | nd | 160 | | 80 | |
| Pep2 | nd | 170 | | 80 | |
| Pep3 | nd | 190 | | 95 | |
| Pep4 | nd | 200 | | 100 | |
| Pep5 | nd | 460 | | 230 | |
| Pep6 | 5 | 50 | 0.1 | 25 | 0.2 |
| Pep7 | 14 | 30 | 0.5 | 13 | 1 |
| Pep8 | 160 | 9 | 18 | 4 | 40 |
| Pep9 | nd | 100 | | 100 | |
| Pep10 | 150 | 25 | 6 | 13 | 12 |
| Pep11 | 840 | 7 | 120 | 3 | 280 |
| Nisin | nd | 9 | | 5 | | nd: not detectable at the maximal concentration tested (1 mg/mL, 300 to 900 μM).
$H_{50}$ is the peptide concentration at which half of the human erythrocytes are lysed.
MIC is the peptide concentration at which bacterial growth is inhibited. 20 mM EDTA was added to Nisin for tests against *E. coli*.

Derived from the sequence of Pep4 without serine, a linear pseudopeptide, Pep9, containing an aza-β³ homohydroxythreonine replacing a threonine was synthesized and tested. Compared to Pep4, the Pep9 hybrid pseudopeptide possesses a two-fold lower MIC against *S. aureus*, but a similar activity against *E. coli*. Pep9 did not trigger detectable lysis of the human erythrocytes. Pep10 (which corresponds to Pep9 after cyclization) was found to possess four- and seven-fold lower MICs against *S. aureus* and *E. coli* bacteria, respectively, compared to Pep9, while remaining slightly hemolytic against human erythrocytes. Compared to Pep10, Pep11 (which lacks the leucine residue) was found to be ~six-fold less hemolytic and to possess a ~four-fold higher antibacterial activity against our two model bacteria, with an activity comparable to that of Nisin, used as an internal positive control. Furthermore, heptapeptide Pep11 was bactericidal at concentrations just above the MIC (8 and 16 μM for *E. coli* and *S. aureus*, respectively) with a therapeutic index beyond $10^2$, suggesting that Pep11 is a very promising antibiotic candidate.

Elevated Stability of the Cyclic Pseudopeptides in Human Sera.

The different peptides were incubated with human serum up to 10 hours, and their stability was analyzed and their half-lives determined by RP-HPLC (FIG. 1). As internal controls, the half-lives of Melittin and Nisin peptides were determined and they are both very short (3.5±0.5 min and 4.5±0.5 min, respectively). PepA1, Pep2 and Pep4 linear peptides were found very unstable in human serum, half degraded after 2 to 3 minutes incubation (FIG. 1). Compared with linear Pep4, its cyclic form (Pep6) has a highly significant, ~320-fold, stabilizing effect. Remarkably, the most active peptide from the series, cyclic Pep11, has a ~240-fold higher stability in human serum than the PepA1 parental peptide (FIG. 1), implying its potential as a novel antibacterial.

Mechanisms of Peptide-Induced Bacterial Killing.

Figure 2:
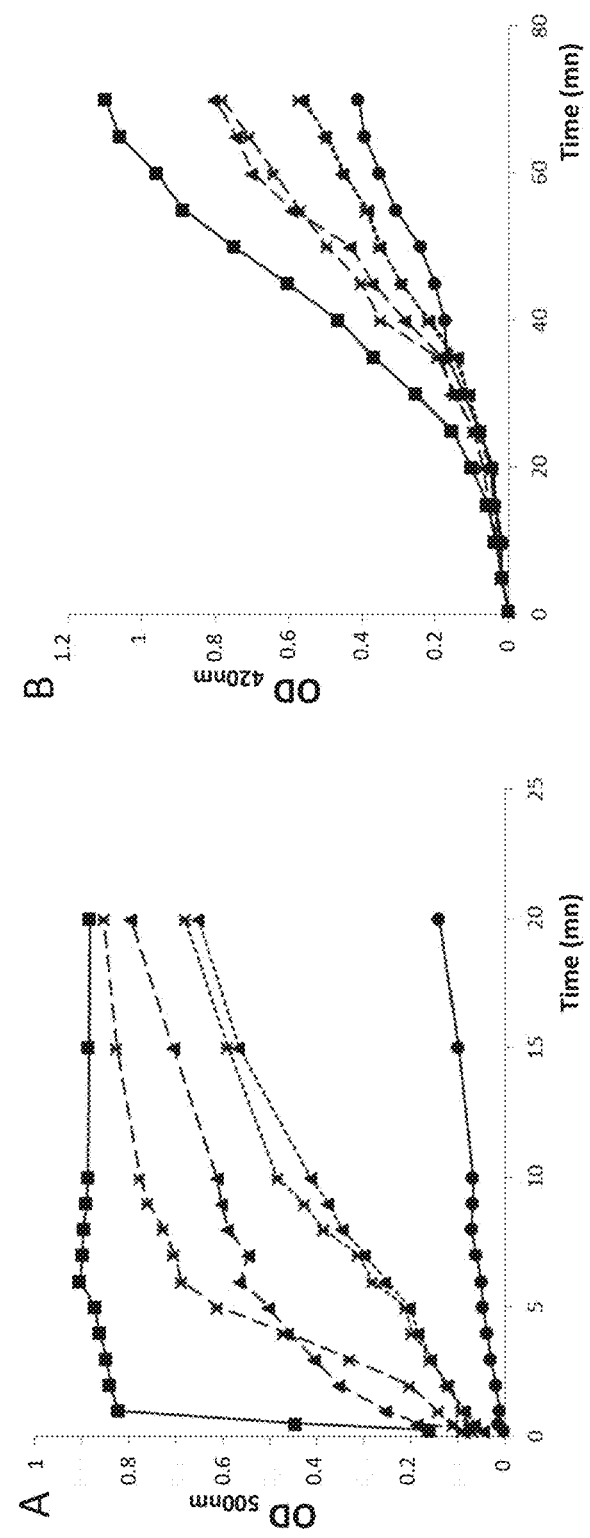
FIG. 2. The native and lead peptides both permeabilize the *E. coli* outer and inner membranes. Concurrent measurements of outer (A) and inner (B) *E. coli* membrane permeation assays by PepA1 and Pep11. (A) Detections of nitrocefin degradation products triggered by a periplasmic β-lactamase. (B) Detections of ONPG degradation products produced by a cytoplasmic β-galactosidase. PepA1 (triangles) and Pep11 (stars) concentrations were 6 μM (dotted lines) and 12 μM (dashed lines) against $10^5$ cfu/mL. Solid lines with squares represent activity of polymixin B at 8 μM. Solid lines with filled circles represent the untreated cells. The mean values of three independent experiments are presented.

The ability of the original (PepA1) and engineered, lead peptide (Pep11) to permeate the *E. coli* outer and inner membranes was monitored through chromogenic reporters, as described (Junkes et al., Eur. Biophys. J., 2011, 40: 515-528). The original 30-residue linear PepA1 and Pep11 cyclic peptide, both permeate the outer and inner membranes of *E. coli* cells, and their activities are comparable (FIG. 2). In Gram positive *S. aureus*, PepA1 localizes at the bacterial membrane and triggers cell death (Sayed et al., Biol. Chem., 2012, 287: 43454-43463). These data indicate that PepA1 also possesses the ability to permeate each membrane of Gram negative bacteria. Compared to polymixin B, used as positive control, the actions of PepA1 and Pep11 on membrane permeation are less efficient. Concerning the outer membrane, the detection of the reporter occurs after 30 seconds with polymixin B and only after 2 to 3 minutes for PepA1 and Pep11. For the inner membrane, the reporter was detected after 20 minutes with polymixin B and 35-40 minutes for PepA1 and Pep11 (FIG. 2). Linear PepA1 and cyclic Pep11, although structurally different, had similar efficiencies on the *E. coli* membranes, that correlate with the MIC results. PepA1 and Pep11 abilities to permeate bacterial membranes sustain their bactericidal effect, as they both destabilize the inner membranes and make them leaky.

Structural Changes of the Bacterial and Human Cells Triggered by the Native and Lead Peptides.

Figure 3:
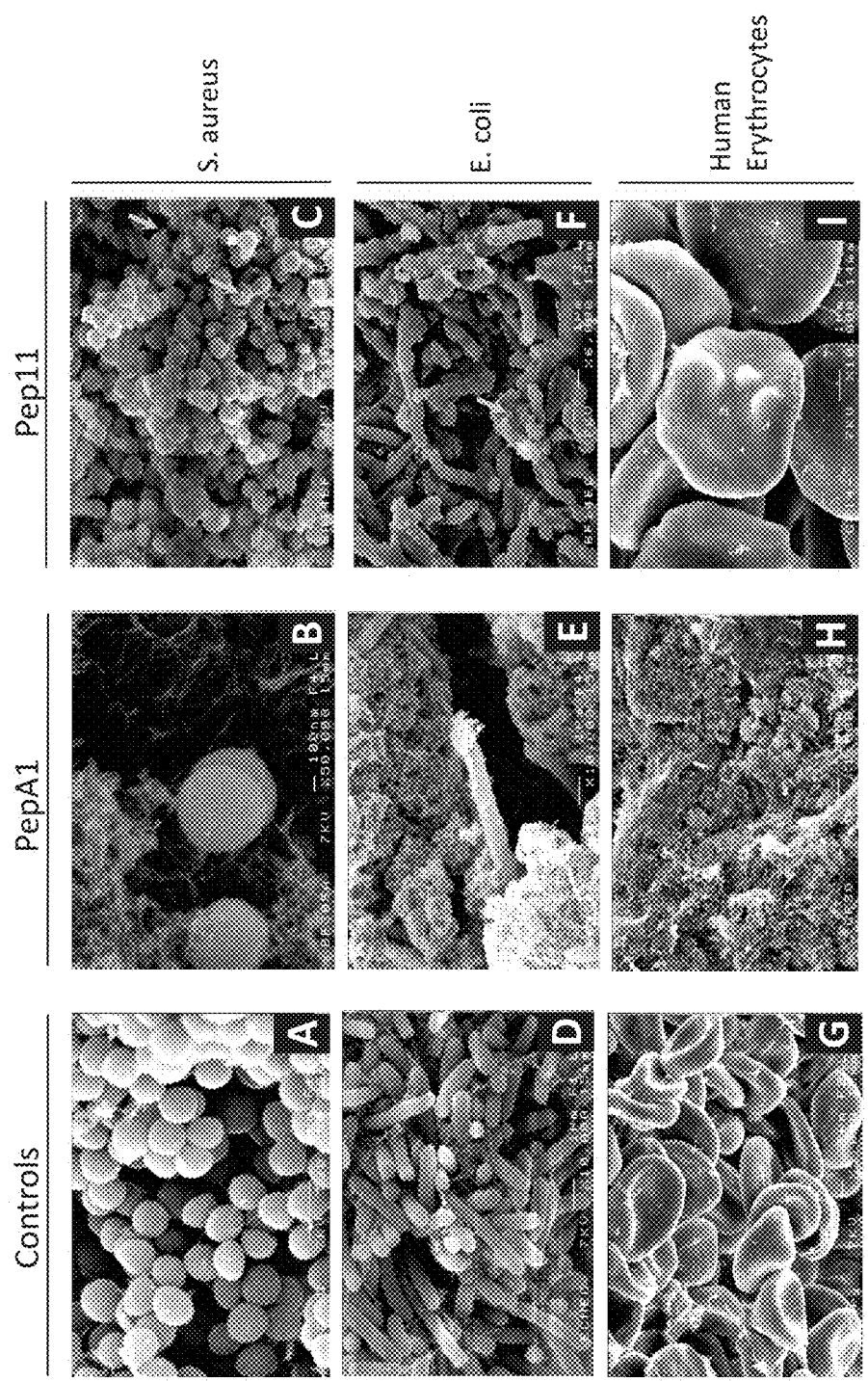
FIG. 3. Damages of bacterial and human cell envelopes by PepA1 and Pep11 revealed by Scanning Electron Microscopy. Micrographs of *S. aureus* (A-C), *E. coli* (D-F) and human erythrocytes (G-I). *S. aureus* or *E. coli* cells were grown in MH stopped at the exponential growth phase ($OD_{600nm}$: 0.5 $10^8$ cfu/mL), kept two hours at room temperature. The human red blood cells in PBS, suspension is 3-4% RBC, also were kept 2 hours at room temperature. The *S. aureus* or *E. coli* cells were exposed to sub-MIC of either PepA1 (6 μM against $10^5$ cfu/mL) or Pep11 (6 μM for *S. aureus* and 2 μM for *E. coli*, respectively against $10^5$ cfu/mL). The human erythrocytes were exposed to 50 μM of PepA1 and 160 μM of Pep11 (corresponding to 0.2 mg/mL for both peptides). Sub-MIC of Pep11 induced cell fusions and the presence of blisters on the surfaces of the *S. aureus* and *E. coli* cells (blue arrows). For the two bacteria, PepA1 was found to induce the release of the cytoplasmic content, as observed with nisin against *S. aureus* (not shown).
Figure 4:
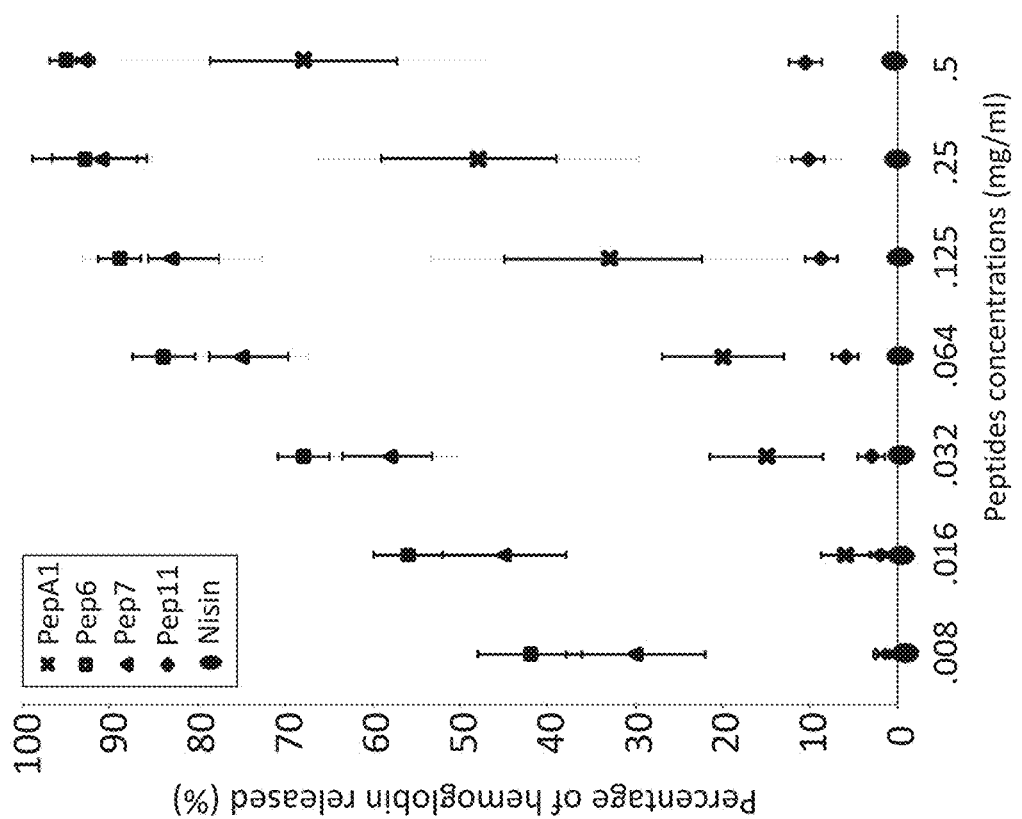
FIG. 4. PepA1 derivatives with reduced lytic activities against human erythrocytes. The data values presented are the mean values of triplicates from three different human blood samples and the standard deviation of the mean are indicated.

For detailed mechanistic insights into peptides functions and actions on membranes, Scanning Electron Microscopy (SEM) was performed. SEM was used to examine the structural changes induced by the cyclic antimicrobial peptide leader (Pep11) onto *E. coli*, *S. aureus* and human red blood cells, to provide mechanistic insights into its function. Analysis of PepA1 actions onto these cells was also performed, as a control. SEM micrographs of untreated *S. aureus*, *E. coli* and human red blood cells were respectively ~0.5, 2 and 6 μm long and displayed smooth and intact surfaces (FIG. 3, controls). After incubations with sub-MIC of PepA1, bacterial cells were damaged, with the presence of many burst cells with their intracellular contents released outside (FIG. 3, PepA1). The same results were observed with human erythrocytes, as expected for a bacterial toxin, with significant hemoglobin discharge at low peptide concentrations (FIG. 4). Interestingly, after incubating *E. coli* and *S. aureus* cells with sub-MIC of Pep11, multiple blisters of various shapes were detected on the cell surfaces (FIG. 3, Pep11). SEM images reveal that Pep11 damages the bacterial envelopes, inducing cell fusions, protruding bubbles, vesicle-like bodies, with only minor releases of their intracellular contents. PepA1 atomic structure solved by NMR (Sayed et al., J. Biol. Chem., 2012, 287: 43454-43463) suggests that it triggers. pores formation within biological membranes. Strikingly, Pep11 damages bacterial cells in a similar manner as does the cyclo-decapeptide Gramicidin S, which induces the formation of multiple blisters and bubbles at the *E. coli* and *S. aureus* surfaces (Hartmann et al., Antimicrob. Agents Chemother., 2010, 54: 3132-3142).

Pep 11 is about 12-fold less haemolytic on human erythrocytes than PepA1 (Table 1), independently evidenced by SEM, with PepA1 blasting the erythrocytes, whereas Pep11 does not (FIG. 3). Elevated concentrations of cyclic Pep11 trigger the formation of sporadic bumps at the membranes of very few human erythrocytes (FIG. 3), with minor haemoglobin release only at elevated peptide concentrations (FIG. 4).

The results presented in Table 2 below were obtained in triplicate as described in the case of Table 1 except that the starting concentration was 500 µM/mL instead of 1 mg/mL. The 4 peptides (Pep15, 16, 18 and 19) that were the most active against *S. aureus* Newman and *E. coli* and peptide Pep21 (which was found to exhibit a strong differential activity against Gram negative and Gram positive strains) were tested against an MRSA (methicillin-resistant *S. aureus*) strain, the N315 strain and the VISA (vancomycin intermediate-resistant *S. aureus*) strain, the Mu50 strain. Hemolysis was performed only for the most active peptides against MRSA and VISA (Pep15, 16 and 19) and Pep21. H50 has not been reached at a concentration of 500 µM. If H50 is not known, the IT cannot be precisely calculated and only a minimal value can be calculate (see for example Pep15: 500 (maximal concentration tested)/2 (CMI)=250 minimal).

As shown by Table 2, all the peptides have an activity against the different *S. aureus* strains that is similar to that of nisin. Under the conditions used, all the peptides were less efficient than vancomycin against the VISA strain. However, they were all more efficient than methicillin against the MRSA and VISA strains.

Conclusion

Peptides with efficient antibacterial activities commonly also crush human cells and are subject to accelerated degradations by human and bacterial peptidases, which restrict their clinical uses. In this study, a powerful bacterial toxin targeting human cells was converted into an effective antibacterial, devoid of toxicity on human erythrocytes. The cyclic pseudopeptide, with an optimized FFWRR sequence pattern that is not found in the starting toxin, results in bacterial membrane alteration and permeation, with stability in human serum substantially upgraded, up to several hours.

Multi-drug resistance bacteria represent a sharp dilemma to medicine, generating concern in original antimicrobial strategies. Discovery and optimization of new antibacterial drugs is notoriously difficult and has been stalled for many years. Over the past 25 years, the challenges to antibacterial discovery have kept the output of novel drug classes to extraordinarily low levels. Short antimicrobial peptides are promising candidates for overcoming the critical and accelerating problem of bacterial resistance to currently utilized antibiotics. In the present study, the inventors have laid foundation for the utilization of engineered bacterial toxins as antibacterial agents worthy of development, therefore providing a paradigm for targeting a broad spectrum of pathogens. These toxin-inferred potent antibacterial peptides interact with and permeate the bacterial membranes and are stable in human body fluids.

TABLE 2

Antibacterial activity against different strains of *S. aureus* and *E. coli* and toxicity against human erythrocytes of cyclic or hybrid pseudopeptide derived from Pep11.

| Peptides | Human cells | | S. aureus | | E. Coli | MRSA | VISA |
|---|---|---|---|---|---|---|---|
| | % hemolysis at 500 µM | H50 (µM) | MIC (µM) | TI (H50/MIC) | MIC (µM) | MIC (µM) | MIC (µM) |
| Pep12 | 98 | 220 | 16 | 14 | 16 | nt | nt |
| Pep13 | nt | | 16 | | 8 | nt | nt |
| Pep14 | nt | | 32 | | 32 | nt | nt |
| Pep15 | 3 | nd | 2 | >250 | 2 | 2 | 2 |
| Pep16 | 34 | nd | 4 | >125 | 4 | 4 | 4 |
| Pep17 | nt | | 250 | | 250 | nt | nt |
| Pep18 | nt | | 4 | | 4 | 8 | 8 |
| Pep19 | 7 | nd | 4 | >125 | 4 | 4 | 4 |
| Pep20 | nt | | 16 | | 8 | nt | nt |
| Pep21 | 38 | nd | 8 | >62 | 125 | 8 | 8 |
| Vancomycin | 0.15 | nd | nt | | nt | 32 | 1 |
| Meticillin | 0.12 | nd | nt | | nt | 32 | nd |
| Nisin | 25 | nd | 8 | | 4 (+EDTA) | 8 | 8 | nt: not tested,
nd: not detectable at the maximal concentration tested (500 µM).
MRSA strain is strain *S. aureus* N315.
VISA strain is strain *S. aureus* Mu 50.
*S. aureus* is strain Newman.
*E. coli* is strain K12 XL-Blue.

What is claimed is:

1. A cyclic antimicrobial peptide, wherein said peptide has an amino acid sequence selected from the group consisting of SEQ ID Nos: 2-14.

2. A pharmaceutical composition comprising an effective amount of at least one cyclic antimicrobial peptide according to claim 1 and a pharmaceutically acceptable carrier or excipient.

3. A product comprising at least one cyclic antimicrobial peptide according to claim 1, or a composition thereof, wherein the product is selected from the group consisting of bandages, plasters, sutures, adhesives, wound dressings, implants, contact lenses, cleaning solutions, storage solutions, cleaning products, personal care products, and cosmetics.

* * * * *

SEQUENCE LISTING

```
<160> NUMBER OF SEQ ID NOS: 23

<210> SEQ ID NO 1
<211> LENGTH: 9
<212> TYPE: PRT
<213> ORGANISM: Artificial Sequence
<220> FEATURE:
<223> OTHER INFORMATION: Cyclic Pep6

<400> SEQUENCE: 1

Phe Phe Trp Leu Ser Arg Arg Thr Lys
1               5

<210> SEQ ID NO 2
<211> LENGTH: 8
<212> TYPE: PRT
<213> ORGANISM: Artificial Sequence
<220> FEATURE:
<223> OTHER INFORMATION: Cyclic Pep7

<400> SEQUENCE: 2

Phe Phe Trp Ser Arg Arg Thr Lys
1               5

<210> SEQ ID NO 3
<211> LENGTH: 7
<212> TYPE: PRT
<213> ORGANISM: Artificial Sequence
<220> FEATURE:
<223> OTHER INFORMATION: Cyclic Pep8

<400> SEQUENCE: 3

Phe Phe Trp Arg Arg Thr Lys
1               5

<210> SEQ ID NO 4
<211> LENGTH: 8
<212> TYPE: PRT
<213> ORGANISM: Artificial Sequence
<220> FEATURE:
<223> OTHER INFORMATION: Cyclic Pep10
<220> FEATURE:
<221> NAME/KEY: MISC_FEATURE
<222> LOCATION: (7)..(7)
<223> OTHER INFORMATION: aza-beta3-hydroxylthreonine

<400> SEQUENCE: 4

Phe Phe Trp Leu Arg Arg Xaa Lys
1               5

<210> SEQ ID NO 5
<211> LENGTH: 7
<212> TYPE: PRT
<213> ORGANISM: Artificial Sequence
<220> FEATURE:
<223> OTHER INFORMATION: Cyclic Pep11
<220> FEATURE:
<221> NAME/KEY: MISC_FEATURE
<222> LOCATION: (6)..(6)
<223> OTHER INFORMATION: aza-beta3-hydroxylthreonine

<400> SEQUENCE: 5

Phe Phe Trp Arg Arg Xaa Lys
1               5

<210> SEQ ID NO 6
<211> LENGTH: 7
<212> TYPE: PRT
```

```
<213> ORGANISM: Artificial Sequence
<220> FEATURE:
<223> OTHER INFORMATION: Cyclic Pep12
<220> FEATURE:
<221> NAME/KEY: MISC_FEATURE
<222> LOCATION: (1)..(1)
<223> OTHER INFORMATION: aza- beta3-1-naphthylalanine
<220> FEATURE:
<221> NAME/KEY: MISC_FEATURE
<222> LOCATION: (6)..(6)
<223> OTHER INFORMATION: aza-beta3-hydroxylthreonine

<400> SEQUENCE: 6

Xaa Phe Trp Arg Arg Xaa Lys
1               5

<210> SEQ ID NO 7
<211> LENGTH: 8
<212> TYPE: PRT
<213> ORGANISM: Artificial Sequence
<220> FEATURE:
<223> OTHER INFORMATION: Cyclic Pep13
<220> FEATURE:
<221> NAME/KEY: MISC_FEATURE
<222> LOCATION: (3)..(3)
<223> OTHER INFORMATION: aza- beta3-1-naphthylalanine
<220> FEATURE:
<221> NAME/KEY: MISC_FEATURE
<222> LOCATION: (7)..(7)
<223> OTHER INFORMATION: aza-beta3-hydroxylthreonine

<400> SEQUENCE: 7

Phe Phe Xaa Trp Arg Arg Xaa Lys
1               5

<210> SEQ ID NO 8
<211> LENGTH: 7
<212> TYPE: PRT
<213> ORGANISM: Artificial Sequence
<220> FEATURE:
<223> OTHER INFORMATION: Cyclic Pep14
<220> FEATURE:
<221> NAME/KEY: MISC_FEATURE
<222> LOCATION: (1)..(1)
<223> OTHER INFORMATION: aza- beta3-2-naphthylalanine
<220> FEATURE:
<221> NAME/KEY: MISC_FEATURE
<222> LOCATION: (3)..(3)
<223> OTHER INFORMATION: aza- beta3-2-naphthylalanine
<220> FEATURE:
<221> NAME/KEY: MISC_FEATURE
<222> LOCATION: (6)..(6)
<223> OTHER INFORMATION: aza-beta3-hydroxylthreonine

<400> SEQUENCE: 8

Xaa Phe Xaa Arg Arg Xaa Lys
1               5

<210> SEQ ID NO 9
<211> LENGTH: 7
<212> TYPE: PRT
<213> ORGANISM: Artificial Sequence
<220> FEATURE:
<223> OTHER INFORMATION: Cyclic Pep15
<220> FEATURE:
<221> NAME/KEY: MISC_FEATURE
<222> LOCATION: (3)..(3)
<223> OTHER INFORMATION: aza- beta3-2-naphthylalanine
<220> FEATURE:
<221> NAME/KEY: MISC_FEATURE
<222> LOCATION: (6)..(6)
<223> OTHER INFORMATION: aza-beta3-hydroxylthreonine
```

```
<400> SEQUENCE: 9

Phe Phe Xaa Arg Arg Xaa Lys
1               5

<210> SEQ ID NO 10
<211> LENGTH: 7
<212> TYPE: PRT
<213> ORGANISM: Artificial Sequence
<220> FEATURE:
<223> OTHER INFORMATION: Cyclic Pep16
<220> FEATURE:
<221> NAME/KEY: MISC_FEATURE
<222> LOCATION: (1)..(1)
<223> OTHER INFORMATION: aza- beta3-2-naphthylalanine
<220> FEATURE:
<221> NAME/KEY: MISC_FEATURE
<222> LOCATION: (3)..(3)
<223> OTHER INFORMATION: aza- beta3-2-naphthylalanine
<220> FEATURE:
<221> NAME/KEY: MISC_FEATURE
<222> LOCATION: (6)..(6)
<223> OTHER INFORMATION: aza-beta3-valine

<400> SEQUENCE: 10

Xaa Phe Xaa Arg Arg Xaa Lys
1               5

<210> SEQ ID NO 11
<211> LENGTH: 7
<212> TYPE: PRT
<213> ORGANISM: Artificial Sequence
<220> FEATURE:
<223> OTHER INFORMATION: Cyclic Pep17
<220> FEATURE:
<221> NAME/KEY: MISC_FEATURE
<222> LOCATION: (1)..(1)
<223> OTHER INFORMATION: aza- beta3-1-naphthylalanine
<220> FEATURE:
<221> NAME/KEY: MISC_FEATURE
<222> LOCATION: (3)..(3)
<223> OTHER INFORMATION: aza- beta3-1-naphthylalanine
<220> FEATURE:
<221> NAME/KEY: MISC_FEATURE
<222> LOCATION: (6)..(6)
<223> OTHER INFORMATION: glycol-amino acid having the chemical
      structure (I)

<400> SEQUENCE: 11

Xaa Phe Xaa Arg Arg Xaa Lys
1               5

<210> SEQ ID NO 12
<211> LENGTH: 7
<212> TYPE: PRT
<213> ORGANISM: Artificial Sequence
<220> FEATURE:
<223> OTHER INFORMATION: Cyclic Pep18

<400> SEQUENCE: 12

Phe Phe Trp Arg Arg Val Lys
1               5

<210> SEQ ID NO 13
<211> LENGTH: 7
<212> TYPE: PRT
<213> ORGANISM: Artificial Sequence
<220> FEATURE:
<223> OTHER INFORMATION: Cyclic Pep19
<220> FEATURE:
<221> NAME/KEY: MISC_FEATURE
<222> LOCATION: (1)..(1)
```

```
<223> OTHER INFORMATION: aza- beta3-1-naphthylalanine
<220> FEATURE:
<221> NAME/KEY: MISC_FEATURE
<222> LOCATION: (3)..(3)
<223> OTHER INFORMATION: aza- beta3-1-naphthylalanine

<400> SEQUENCE: 13

Xaa Phe Xaa Arg Arg Val Lys
1               5

<210> SEQ ID NO 14
<211> LENGTH: 7
<212> TYPE: PRT
<213> ORGANISM: Artificial Sequence
<220> FEATURE:
<223> OTHER INFORMATION: Cyclic Pep20
<220> FEATURE:
<221> NAME/KEY: MISC_FEATURE
<222> LOCATION: (1)..(1)
<223> OTHER INFORMATION: aza- beta3-phenylalanine
<220> FEATURE:
<221> NAME/KEY: MISC_FEATURE
<222> LOCATION: (3)..(3)
<223> OTHER INFORMATION: aza- beta3-1-naphthylalanine
<220> FEATURE:
<221> NAME/KEY: MISC_FEATURE
<222> LOCATION: (6)..(6)
<223> OTHER INFORMATION: aza-beta3-hydroxylthreonine

<400> SEQUENCE: 14

Xaa Phe Xaa Arg Arg Xaa Lys
1               5

<210> SEQ ID NO 15
<211> LENGTH: 30
<212> TYPE: PRT
<213> ORGANISM: Artificial Sequence
<220> FEATURE:
<223> OTHER INFORMATION: PepA1

<400> SEQUENCE: 15

Met Leu Ile Phe Val His Ile Ile Ala Pro Val Ile Ser Gly Cys Ala
1               5                   10                  15

Ile Ala Phe Phe Ser Tyr Trp Leu Ser Arg Arg Asn Thr Lys
            20                  25                  30

<210> SEQ ID NO 16
<211> LENGTH: 18
<212> TYPE: PRT
<213> ORGANISM: Artificial Sequence
<220> FEATURE:
<223> OTHER INFORMATION: Pep N-Ter

<400> SEQUENCE: 16

Met Leu Ile Phe Val His Ile Ile Ala Pro Val Ile Ser Gly Cys Ala
1               5                   10                  15

Ile Ala

<210> SEQ ID NO 17
<211> LENGTH: 12
<212> TYPE: PRT
<213> ORGANISM: Artificial Sequence
<220> FEATURE:
<223> OTHER INFORMATION: Pep1

<400> SEQUENCE: 17

Phe Phe Ser Tyr Trp Leu Ser Arg Arg Asn Thr Lys
1               5                   10
```

```
<210> SEQ ID NO 18
<211> LENGTH: 11
<212> TYPE: PRT
<213> ORGANISM: Artificial Sequence
<220> FEATURE:
<223> OTHER INFORMATION: Pep2

<400> SEQUENCE: 18

Phe Phe Ser Tyr Trp Leu Ser Arg Arg Thr Lys
1               5                   10

<210> SEQ ID NO 19
<211> LENGTH: 10
<212> TYPE: PRT
<213> ORGANISM: Artificial Sequence
<220> FEATURE:
<223> OTHER INFORMATION: Pep3

<400> SEQUENCE: 19

Phe Phe Ser Trp Leu Ser Arg Arg Thr Lys
1               5                   10

<210> SEQ ID NO 20
<211> LENGTH: 9
<212> TYPE: PRT
<213> ORGANISM: Artificial Sequence
<220> FEATURE:
<223> OTHER INFORMATION: Pep4

<400> SEQUENCE: 20

Phe Phe Trp Leu Ser Arg Arg Thr Lys
1               5

<210> SEQ ID NO 21
<211> LENGTH: 8
<212> TYPE: PRT
<213> ORGANISM: Artificial Sequence
<220> FEATURE:
<223> OTHER INFORMATION: Pep5

<400> SEQUENCE: 21

Phe Phe Trp Leu Ser Arg Thr Lys
1               5

<210> SEQ ID NO 22
<211> LENGTH: 8
<212> TYPE: PRT
<213> ORGANISM: Artificial Sequence
<220> FEATURE:
<223> OTHER INFORMATION: Pep9
<220> FEATURE:
<221> NAME/KEY: MISC_FEATURE
<222> LOCATION: (7)..(7)
<223> OTHER INFORMATION: aza-beta3-hydroxylthreonine

<400> SEQUENCE: 22

Phe Phe Trp Leu Arg Arg Xaa Lys
1               5

<210> SEQ ID NO 23
<211> LENGTH: 7
<212> TYPE: PRT
<213> ORGANISM: Artificial Sequence
<220> FEATURE:
<223> OTHER INFORMATION: Pep21
<220> FEATURE:
<221> NAME/KEY: MISC_FEATURE
```

```
<222> LOCATION: (1)..(1)
<223> OTHER INFORMATION: aza- beta3-2-naphthylalanine
<220> FEATURE:
<221> NAME/KEY: MISC_FEATURE
<222> LOCATION: (3)..(3)
<223> OTHER INFORMATION: aza- beta3-2-naphthylalanine
<220> FEATURE:
<221> NAME/KEY: MISC_FEATURE
<222> LOCATION: (6)..(6)
<223> OTHER INFORMATION: aza- beta3-valine

<400> SEQUENCE: 23

Xaa Phe Xaa Arg Arg Xaa Lys
1               5
```